(12) United States Patent
Azzouz et al.

(10) Patent No.: US 9,802,974 B2
(45) Date of Patent: Oct. 31, 2017

(54) **SYNTHESIS OF DIVERSE GLYCOSYLPHOSPHATIDYLINOSITOL GLYCANS FROM *TOXOPLASMA GONDII* AND THEIR APPLICATION AS VACCINES AND DIAGNOSTICS**

(71) Applicant: Max-Planck-Gesellschaft zur Förderung der Wissenschaften e.V., München (DE)

(72) Inventors: Nahid Azzouz, Berlin (DE); Sebastian Götze, Berlin (DE); Peter H. Seeberger, Klein Machnow (DE); Daniel Varon Silva, Berlin (DE); Yu-Hsuan Tsai, Berlin (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 0 days.

(21) Appl. No.: 14/416,052

(22) PCT Filed: Jul. 23, 2013

(86) PCT No.: PCT/EP2013/065559
§ 371 (c)(1),
(2) Date: Jan. 20, 2015

(87) PCT Pub. No.: WO2014/016317
PCT Pub. Date: Jan. 30, 2014

(65) Prior Publication Data
US 2015/0203523 A1 Jul. 23, 2015

(30) Foreign Application Priority Data

Jul. 24, 2012 (EP) .................................... 12177588

(51) Int. Cl.
*C07H 1/02* (2006.01)
*C07H 15/207* (2006.01)
(Continued)

(52) U.S. Cl.
CPC ......... *C07H 15/207* (2013.01); *A61K 39/002* (2013.01); *A61K 39/012* (2013.01);
(Continued)

(58) Field of Classification Search
CPC ...... C07H 15/207; C07H 1/02; C08B 37/006; A61K 39/012; A61K 39/002;
(Continued)

(56) References Cited

FOREIGN PATENT DOCUMENTS

WO    WO 97/10249 A1    3/1997

OTHER PUBLICATIONS

Debierre-Grockiego, Francoise, Glycolipids are potential targets for protozoan parasite diseases. Trends in Parasitology 2010, vol. 26, pp. 404-411.*

(Continued)

*Primary Examiner* — Shafiqul Haq
(74) *Attorney, Agent, or Firm* — Knobbe Martens Olson & Bear, LLP

(57) ABSTRACT

The present invention relates to the synthesis of GPI-related surface antigens of the parasite *Toxoplasma gondii* (*T. gondii*) and the resulting products obtained. These synthetic compounds are suitable for diagnosis of toxoplasmosis, as well as vaccine against toxoplasmosis, a diseases caused by infection with *T. gondii*.

10 Claims, 16 Drawing Sheets

(51) Int. Cl.
    *A61K 39/002*     (2006.01)
    *A61K 47/48*     (2006.01)
    *G01N 33/569*     (2006.01)
    *A61K 39/012*     (2006.01)
    *C08B 37/00*     (2006.01)
    *A61K 39/00*     (2006.01)

(52) U.S. Cl.
    CPC ......... *A61K 47/48261* (2013.01); *C07H 1/02* (2013.01); *C08B 37/006* (2013.01); *G01N 33/56905* (2013.01); *A61K 2039/55544* (2013.01); *A61K 2039/64* (2013.01); *G01N 2333/45* (2013.01)

(58) Field of Classification Search
    CPC .... A61K 47/48261; A61K 2039/55544; A61K 2039/64; G01N 33/56905; G01N 2333/45
    See application file for complete search history.

(56) References Cited

OTHER PUBLICATIONS

Azzouz et al. Synthetic glycosylphosphatidylinositol as tools for glycoparasitology research. OMICS A Journal of Integrative Biology, 2010, vol. 14, No. 4, pp. 445-454.*

Tsai et al., "A general Method for Synthesis of GPI Anchors Illustrated by the Total Synthesis of the Low-Molecular Weight Antigen from *Toxoplasma gondii*", *Angew. Chem. Int. Ed*. 2011, 50, 9961.

Kwon et al., "Total Syntheses of fully lipidated glycosylphosphatidylinositol anchors of *Toxoplasma gondii*", *Chem. Comm*. 2005, 2280.

Debierre-Grockiego et al., "Activation of TLR2 and TLR4 by Glycosylphosphatidylinositols Derived from *Toxoplasma gondii*", *J. Immunol*. 2007, 179, 1129.

Pekari et al., "Synthesis of the Fiully Phosphorylated GPI Anchor Pseudohexasaccharide of *Toxoplasma gondii*", *J. Org. Chem*. 2001, 66, 7432.

Pekari et al., "*A Variable Concept for the Preparation of Branched Glycosyl Phosphatidyl Inositol Anchors*", *J. Org. Chem*. 2003, 68, 1295.

Kwon et al., "Assembly of a Series of Malarial Glycosylphosphatidylinositol Anchor Oligosaccharides", *Chem. Eur. J*. 2005, 11, 2493.

McCool et al., "B- and T-Cell Immune Responses to Pneumococcal Conjugate Vaccines: Divergence between Carrier- and Polysaccharide-Specific Immunogenicity", *Infect. Immun*. 1999, 67, 4862.

Wittrock et al., "Synthetische Vakzine aus tumorassoziierten Glycopeptidantigenen durch immunkompatible Verankerung uber Thioether an Rinderserumalbumin", *Angew. Chem*. 2007, 119, 5319.

Stillwaggon et al., "Maternal Serologic Screening to Prevent Congenital Toxoplasmosis: A Decision-Analytic Economic Model", *PLOS Negl. Trop. Dis*. 2011, 5(9), 1333.

Tomavo et al., "A Family of Glycolipids from *Toxoplasma gondii*", *J. Biol. Chem*. 1992, 267, 11721.

Kawano et al., "Natural killer-like nonspecific tumor cell lysis mediated by specific ligand-activated Va14 NKT cells", *Proc. Natl. Acad. Sci*. USA, 1998, 95, 5690.

Dao et al., "Unspecific Reactivity of IgM Directed Against the Low-Molecular-Weight Antigen of Toxoplasma gondii", *Eur. J. Microbiol. Infect. Dis*. 2003, 22, 418.

\* cited by examiner

SYNTHESIS OF DIVERSE GLYCOSYLPHOSPHATIDYLINOSITOL GLYCANS FROM *TOXOPLASMA GONDII* AND THEIR APPLICATION AS VACCINES AND DIAGNOSTICS

INCORPORATION BY REFERENCE TO RELATED APPLICATIONS

Any and all priority claims identified in the Application Data Sheet, or any correction thereto, are hereby incorporated by reference under 37 CFR 1.57. This application is the national phase under 35 U.S.C. §371 of prior PCT International Application No. PCT/EP2013/065559 which has an International Filing Date of Jul. 23, 2013, which designates the United States of America, and which claims priority to European Application No. 12177588.6 filed Jul. 24, 2012, the disclosures of which are hereby expressly incorporated by reference in their entirety and are hereby expressly made a portion of this application.

The present invention relates to the synthesis of GPI-related surface antigens of the parasite *Toxoplasma gondii* (*T. gondii*) and the resulting products obtained. These synthetic compounds are suitable for diagnosis of toxoplasmosis, as well as vaccine against toxoplasmosis, a diseases caused by infection with *T. gondii*.

Glycosylphosphatidylinositols (GPIs) are complex glycolipids that are found in eukaryotic cells either attached to the C-terminus of proteins or in free form. These complex glycolipids feature a phosphoethanolamine unit connecting the C-terminus of the protein to the glycan, a conserved pseudopentasaccharide core of $H_2N(CH_2)_2OPO_3H6Man\alpha1\rightarrow2Man\alpha1\rightarrow6Man\alpha1\rightarrow4GlcN\alpha1\rightarrow6myo$-Ino1-$OPO_3H$ and a lipid attached to the core glycan via a phosphodiester linkage. The conserved GPI structure can be further decorated by various substituents including additional phosphoethanolamine units, an additional fatty acid ester at C2 position of myo-inositol and oligosaccharide branch at C3 or C4 of ManI. The constitutive identity of the lipid subunit is variable and may include diacylglycerols, alkylacylglycerols or ceramides, with chains of different length and varying degrees of unsaturation. When GPIs are isolated from natural sources, they are often obtained as heterogeneous mixtures especially in respect to the glycan and lipid subunit. GPIs isolated from different species and, in some cases, from different tissues of the same organism, feature significant structural differences. The primary biological role of GPIs is to localize the attached protein to the outer surface of the plasma membrane bilayer. It is suggested that GPIs are responsible for the association of anchored proteins with lipid rafts and are, thereby, involved in diverse processes such as regulation of innate immunity, protein trafficking, and antigen presentation.

Toxoplasmosis is a parasitic disease caused by the protozoan *Toxoplasma gondii* (*T. gondii*). *T. gondii* is ubiquitous in all warm blooded animals, but the primary host is the family of Felidae. A third to a half of the human population will have a toxoplasmosis infection at some point in their lives, but very few have symptoms. During the first few weeks after exposure, the infection typically causes no symptoms or a mild, flu-like illness: swollen lymph nodes, high temperature or muscle aches. However in most immunocompetent patients, the infection enters a latent phase, during which only bradyzoites are present, forming cysts in nervous and muscle tissues. Thereafter, the parasite rarely causes any symptoms in otherwise healthy adults. Along with, immunosuppression reactivation of a latent infection may occur and manifests primarily as a toxoplasmic encephalitis. Therefore, anyone with a compromised immune system is at risk. These individuals include those undergoing chemotherapy, people suffering from HIV/AIDS or other immune disorders and organ-transplant recipients. The parasite can cause encephalitis (inflammation of the brain) and neurologic diseases, and can affect the heart, liver, inner ears, and eyes. Furthermore, primary infection with *T. gondii* during pregnancy can lead to transmission of the parasite from the mother to the unborn child, leading to a congenital toxoplasmosis. Women infected before conception normally do not transmit toxoplasmosis to the fetus. Nevertheless, there are cases known in which women, who already had a latent toxoplasmosis, got reinfected during pregnancy with a highly virulent strain of *T. gondii* that caused congenital toxoplasmosis. Disease in neonates may be severe, particularly if acquired early in pregnancy. Even spontaneous abortion and stillbirth may occur. Other symptoms that may occur are: low birth weight, fever, jaundice, abnormalities of the retina, mental retardation, hydrocephalus, convulsions, and brain calcification.

Universal screening of pregnant women for example is cost saving at an expected cost of $390 per child screened compared to an expected societal cost of congenital toxoplasmosis of $1010 per birth under the "no maternal screening". Countries such as France that have a high prevalence of toxoplasmosis already established a universal maternal screening program. With an estimated 4 million births per year in the U.S. nearly $2.5 billion could be saved annually compared to no maternal screening (*PLoS Negl Trop Dis.* 2011; 5(9), 1333). The diagnosis of toxoplasmosis can be done using a variety of methods. The difficulty lies in the length of time, which is needed and in determining whether the infection is acute or chronic (latent). Acute infection can best be verified by identifying *T. gondii* parasite or *T. gondii* DNA from the patient's blood. Congenital infection of fetuses can be identified by the presence of cysts in the placenta or fetus. Of particular interest is determining acute infection in pregnant women, due to the risk of congenital toxoplasmosis. An acute toxoplamosis is accompanied by a high titer of IgM and low levels of IgG antibodies against *T. gondii* in the blood of a patient. Since high IgM titers can be persistent and detectable for over one year after the primary infection, it is very difficult to distinguish a latent from an acute toxoplasmosis. There are effective diagnostic techniques that monitor changes in the mother's antibody expression over time, but quick diagnosis is greatly preferred because fetuses often rapidly become infected. The Robert-Koch-Institute recommends a serological diagnosis using three subsequently steps:

1. *Toxoplasma*-antibody screening test: The most commonly used serologic tests detect the presence of anti-*T. gondii* IgG antibodies. IgG antibodies can be detected with the Sabin-Feldman dye test (considered the gold standard), indirect fluorescent antibody (IFA) or agglutination. If tests applied to specific total antibodies against *T. gondii* as well as to IgG antibodies are negative, then there is neither an infection, nor immunity. If the test for total antibodies is negative an infection can be ruled out. Because screening tests based on IgG used in the early phase of infection can still be negative, they must be supplemented especially in pregnant women with an IgM test.

2. *Toxoplasma* IgM antibody test: If such test results are negative (but positive IgG-Ab test) it can be assumed that an inactive (latent) toxoplasma infection exists. Further studies are not required. If the test is positive further evaluation must be done, especially during pregnancy or if differentiated clinical symptoms exists.

3. *Toxoplasma* fact-finding process: This includes in particular the determination of the avidity of IgG antibodies, the IgA antibody detection, immunoblot and quantitative research methods. Such a further determination using PCR and histological tests is very expensive.

Hence, the diagnosis of *T. gondii* infection, especially of acute toxoplasmosis during pregnancy, is still difficult and time consuming. Therefore, there is need for an effective diagnostic test, which allows a fast and reliable diagnosis.

From epidemiological view, the prevention of infection is the most important. It is essential to prevent a primary infection during pregnancy. For this it is necessary to know whether there is immunity or not. So far, the only possibility for prevention is to avoid acquisition of *T. gondii* infection. These persons should avoid contact with materials that may be contaminated with cat feces and the contact with raw meat. The development of a vaccine based on a defined antigen against *T. gondii*, which produces a sterile immunity is therefore of highest interest. In the last 60 years, numerous studies aimed at developing a vaccine against *T. gondii*. However, all these approaches were based on live or inactivated parasites, purified or recombinant proteins, or plasmids encoding protein antigens, and failed to induce protection in mouse models. While some of these antigens increased survival in challenged mice and reduced brain cyst loads, they proved unsuccessful in inhibition of maternal-fetal transmission.

To meet these challenges, the inventors focused on another class of immunogenic molecules, the GPI anchors, contained by the cell membrane of *T. gondii*. The two GPIs contained by the cell membrane of *T. gondii* differ only by the presence of an additional α-glucose (α-Glc) in the side chain. While one GPI is used as a membrane anchor for proteins and surface antigens of the parasite, the GPI containing the additional α-Glc in the side chain is a free glycolipid on the plasma membrane and is also known as the low molecular weight antigen of *T. gondii* that elicits a specific IgM immune response in humans during an acute toxoplasmosis. Both GPIs of *T. gondii* stimulate the production of the cytokine TNF-α in macrophages. Hence, the GPIs of *T. gondii* seem to be promising candidates for the development of a vaccine and a diagnostic test.

The use of the GPIs as antigens for the development of a vaccine against *T. gondii* eliminates the risk of causing toxoplamosis associated with a vaccine based on attenuated or inactivated parasites. Moreover, *T. gondii* displays a high antigenic variation and passes through various life cycles, for which reason protein-based vaccines could be rendered ineffective through mutations. Since the biosynthesis of carbohydrates is not template-driven, resistance against the vaccines of this invention is not expected. In addition, protein or DNA-based vaccines are very likely limited to induce protective immunity against all strains of the parasite, but the GPI containing the additional α-Glc on the side chain is most probably common in every genotype.

Due to heterogeneity of GPIs isolated from biological samples and their amphiphilic character, which renders purification of GPI structures challenging, homogeneous samples of these glycolipids are only accessible via chemical synthesis. Further literature shows that isolated GPI structures contain also other glycolipids, which could cause false positive results (*Eur. J. Clin. Microbiol. Infect. Dis.*, 2003, 22, 418). With this in mind, the inventors initiated a synthetic program to address the need for a diverse set of homogeneous GPIs and their analogues as a basis for vaccines and diagnostic devices.

Therefore, the objective of the present invention is to provide a synthesis of defined compounds derived from GPIs of *T. gondii*, where the resulting products are suitable for use in a diagnostic test of toxoplasmosis and for covalent linkage to a carrier for use as a vaccine for humans and animals against diseases caused by infection with *T. gondii*. The vaccines described herein are directed against a large spectrum of parasite strains. Further preferred embodiments of the present invention are disclosed in the dependent claims, the description and the examples.

DESCRIPTION OF THE INVENTION

As used herein, the term "bifunctional linker" refers to a bifunctional molecule containing functional group X and functional group Y, wherein functional group X is capable of reacting with the terminal thiol group of the compounds of general formula (I) and the functional group Y is capable of reacting with a carrier.

Saccharides are known by the person skilled in the art as TI-2 (T cell independent-2) antigens and poor immunogens. Therefore, to produce a saccharide-based vaccine, said saccharides are linked or conjugated to a "carrier" to provide a conjugate, which presents an increased immunogenicity in comparison with the saccharide. As used herein, a carrier is a pharmacological or immunological agent that modifies the effect of other agents, such as an active agent or vaccine. The term "carrier" as used herein refers to a compound used as a carrier protein, to which a compound of general formula (I) is linked and which enhances the recipient's immune response to the compound of general formula (I). In a preferred embodiment, the term "carrier" as used herein refers to a glycosphingolipid with immunomodulatory properties, to which a compound of general formula (I) is linked and which enhances the recipient's immune response to the compound of general formula (I).

The term "conventional pharmaceutically acceptable adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples immunological adjuvants include, but are not restricted to oil emulsions (e.g., Freund's adjuvant), saponins, aluminium or calcium salts (e.g., alum), non-ionic block polymer surfactants, and many others.

Thus, the present invention relates to compounds of general formula (I)

(I)

[Chemical structure of compound of general formula (I) showing a complex saccharide structure with substituents $R^1$, $R^2$, $R^3$, $R^4$, and OR groups]

wherein

R represents —H, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, -Ph, —CH₂-Ph, or

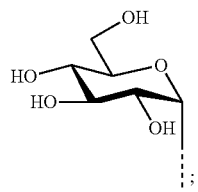

$R^1$ and $R^4$ represent independently of each other —OH, or —OP(O)(OH)—O—X—NH₂;

X represents —CH₂—, —C₂H₄—, $R^2$ represents —SO₂($R^5$), —OSO₂($R^5$), —OSO₂(O$R^5$), or —OP(O)(O$R^5$)(O$R^6$);

$R^3$ represents —H, —OH, —NH₂, —NHCOCH₃, —NHCOCH₂CH₃, —NHCOCH₂CH₂CH₃ or —N₃;

$R^5$ and $R^6$ represent independently of each other —H, -L-SH, —(C₂H₄O)$_r$—CH₂—SH or —(C₂H₄O)$_r$—C₂H₄—SH and $R^5$ and $R^6$ cannot be simultaneously —H;

L represents a linker;

and r is an integer from 1 to 40.

Preferably one of $R^5$ and $R^6$ is hydrogen, and more preferably $R^6$ is hydrogen. Thus, $R^2$ represents preferably —SO₂($R^5$), —OSO₂($R^5$), —OSO₂(O$R^5$), or —OP(O)(O$R^5$)(OH).

Instead of using the disclaimer in the definition of $R^5$ and $R^6$, $R^5$ and $R^6$ can be defined as follows: $R^5$ represents -L-SH, —(C₂H₄O)$_r$—CH₂—SH or —(C₂H₄O)$_r$—C₂H₄—SH and $R^6$ represents —H, -L-SH, —(C₂H₄O)$_r$—CH₂—SH or —(C₂H₄O)$_r$—C₂H₄—SH.

Preferred are compounds of general formula (I), wherein R and $R^1$ to $R^4$, L, X and r have the meaning as disclosed herein and especially the meanings as disclosed above and wherein $R^6$ represents hydrogen and $R^5$ represents -L-SH, —(C₂H₄O)$_r$—CH₂—SH or —(C₂H₄O)$_r$—C₂H₄—SH and more preferred $R^5$ represents -L-SH.

Even more preferred are compounds of general formula (I), wherein $R^2$ represents —SO₂(L-SH), —OSO₂(L-SH), —OSO₂(O-L-SH), or —OP(O)(O-L-SH)(OH) and still more preferred wherein $R^2$ represents —OSO₂(O-L-SH), or —OP(O)(O-L-SH)(OH) and most preferred wherein $R^2$ represents —OP(O)(O-L-SH)(OH).

In above formula (I), L represents any suitable linker. Preferably L represents a linker containing up to 50 carbon atoms. Further preferred is that this linker L is linked through a carbon atom of the linker to the SH group and through the same or preferably another carbon atom of the linker to the —SO₂—, —OSO₂—, —OSO₂—O— or the phosphate group —OP(O)(O—)(O—) in the residues —SO₂-L-SH, —OSO₂-L-SH, —OSO₂—O-L-SH, —OP(O)(OH)(O-L-SH) or —OP(O)(O-L-SH)(O-L-SH). This carbon atom linked linker contains up to 50 carbon atoms and preferably up to 40 carbon atoms and more preferably between 3 and 35 carbon atoms and most preferably between 5 and 30 carbon atoms.

More preferably L represents -$L^1$-$L^2$-$L^3$-, -$L^1$-$L^3$-, -$L^1$-, or -$L^1$-$L^2$-$L^4$-$L^5$-$L^3$-, wherein $L^1$ and $L^4$ represent independently of each other —(CH₂)$_n$—, —(CH₂)$_m$—, —CHR⁷—(CH₂)$_m$—, —(CH₂)$_n$—CR⁷R⁸—(CH₂)$_m$—, -o-C₆H₄—, -m-C₆H₄—, -p-C₆H₄—;

$L^2$ and $L^5$ represent independently of each other —(CH₂)$_p$—, —(CH₂)$_q$—, —CHR⁹—, —CR⁹R¹⁰—, —O—, —S—, —CO—, —COO—, —O—CO—, —NH—CO—, —CO—NH—, —NH—CO—NH—, -o-C₆H₄—, -m-C₆H₄—, -p-C₆H₄—, —NR¹¹—, —CH=CH—;

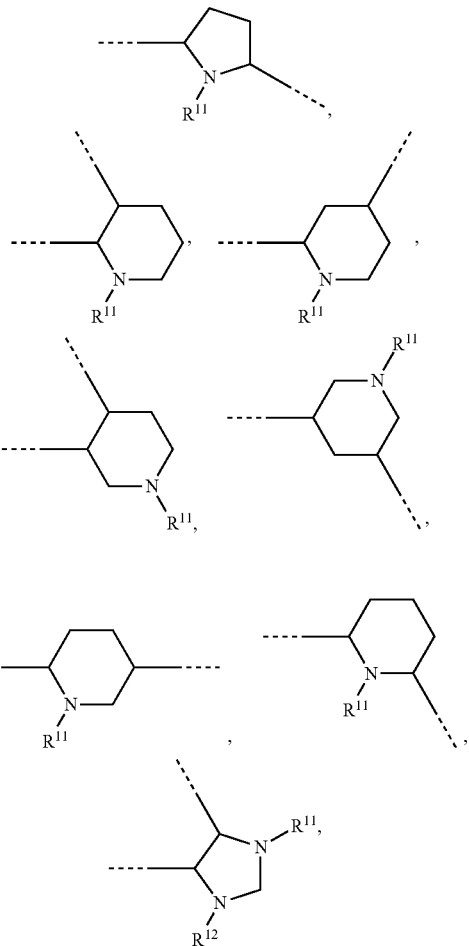

$L^3$ represents —(CH₂)$_r$—, —(CH₂)$_r$—CR¹³R¹⁴—(CH₂)$_s$—, -o-C₆H₄—, -m-C₆H₄—, -p-C₆H₄—;

Compounds of general formula (I) are more preferred, wherein $R^2$ represents —SO₂(-$L^1$-$L^2$-$L^3$-SH), —OSO₂(-$L^1$-$L^2$-$L^3$-SH), —OSO₂(O-$L^1$-$L^2$-$L^3$-SH), or —OP(O)(O-$L^1$-$L^2$-$L^3$-SH)(OH) and still more preferred wherein $R^2$ represents —OSO₂(O-$L^1$-$L^2$-$L^3$-SH), or —OP(O)(O-$L^1$-$L^2$-$L^3$-SH)(OH) and most preferred wherein $R^2$ represents —OP(O)(O-$L^1$-$L^2$-$L^3$-SH)(OH) and again even more preferred are compounds of general formula (I), wherein $R^2$ represents —SO₂(-$L^1$-$L^3$-SH), —OSO₂(-$L^1$-$L^3$-SH), —OSO₂(O-$L^1$-$L^3$-SH), or —OP(O)(O-$L^1$-$L^3$-SH)(OH) and still more preferred wherein $R^2$ represents —OSO₂(O-$L^1$-$L^3$-SH), or —OP(O)(O-$L^1$-$L^3$-SH)(OH) and most preferred wherein $R^2$ represents —OP(O)(O-$L^1$-$L^3$-SH)(OH) and again even more preferred are compounds of general formula (I), wherein $R^2$ represents —$SO_2$(-$L^1$-SH), —$OSO_2$(-$L^1$-SH), —$OSO_2$(O-$L^1$-SH), or —OP(O)(O-$L^1$-SH)(OH) and still more preferred wherein $R^2$ represents —$OSO_2$(O-$L^1$-SH), or —OP(O)(O-$L^1$-SH)(OH) and most preferred wherein $R^2$ represents —OP(O)(O-$L^1$-SH)(OH).

In these compounds wherein $R^2$ has the meaning as defined in the afore-mentioned paragraph it is moreover preferred that $R^1$ represents —OH and/or that $R^4$ represents —OP(O)(OH)—O—X—$NH_2$ and especially —OP(O)(OH)—O—$CH_2$—$CH_2$—$NH_2$.

$R^7$ to $R^{10}$, $R^{13}$ and $R^{14}$ represent independently of each other —H, —$NH_2$, —OH, —$OCH_3$, —$OC_2H_5$, —$OC_3H_7$, cyclo-$C_3H_5$, cyclo-$C_4H_7$, cyclo-$C_5H_9$, cyclo-$C_6H_{11}$, cyclo-$C_7H_{13}$, cyclo-$C_8H_{15}$, -Ph, —$CH_2$-Ph, —$CPh_3$, —$CH_3$, —$C_2H_5$, —$C_3H_7$, —$CH(CH_3)_2$, —$C_4H_9$, —$CH_2$—CH$(CH_3)_2$, —CH($CH_3$)—$C_2H_5$, —C($CH_3$)$_3$, —CH($CH_3$)—$C_3H_7$, —$CH_2$—CH($CH_3$)—$C_2H_5$, —CH($CH_3$)—CH$(CH_3)_2$, —C($CH_3$)$_2$—$C_2H_5$, —$CH_2$—C($CH_3$)$_3$, —CH$(C_2H_5)_2$, —$C_2H_4$—CH($CH_3$)$_2$, —$C_6H_{13}$, —$C_3H_6$—CH$(CH_3)_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH$(CH_3)_2$, —CH($CH_3$)—CH($CH_3$)—$C_2H_5$, —$CH_2$—CH$(CH_3)$—CH$(CH_3)_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —CH=$CH_2$, —$CH_2$—CH=$CH_2$, —C($CH_3$)=$CH_2$, —CH=CH—$CH_3$, —$C_2H_4$—CH=$CH_2$, —$C_7H_{15}$, —$C_8H_{17}$, —$CH_2$—CH=CH—$CH_3$, —CH=CH—$C_2H_5$, —$CH_2$—C($CH_3$)=$CH_2$, —CH($CH_3$)—CH=CH, —CH=C($CH_3$)$_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —$CH_2NH_2$, —$CH_2OH$, —$CH_2$—$CH_2NH_2$, —$C_6H_4$—$OCH_3$, —$C_6H_4$—OH, —$CH_2$—$CH_2$—$OCH_3$, —$CH_2$—$CH_2OH$, —$CH_2$—$OCH_3$, —$CH_2$—$C_6H_4$—$OCH_3$, —$CH_2$—$C_6H_4$—OH, $R^{11}$ and $R^{12}$ represent independently of each other cyclo-$C_3H_5$, cyclo-$C_4H_7$, cyclo-$C_5H_9$, cyclo-$C_6H_{11}$, cyclo-$C_7H_{13}$, cyclo-$C_8H_{15}$, -Ph, —$CH_2$-Ph, —$CPh_3$, —$CH_3$, —$C_2H_5$, —$C_3H_7$, —CH($CH_3$)$_2$, —$C_4H_9$, —$CH_2$—CH$(CH_3)_2$, —CH$(CH_3)$—$C_2H_5$, —C($CH_3$)$_3$, —$C_5H_{11}$, —CH($CH_3$)—$C_3H_7$, —$CH_2$—CH($CH_3$)—$C_2H_5$, —CH($CH_3$)—CH$(CH_3)_2$, —C($CH_3$)$_2$—$C_2H_5$, —$CH_2$—C($CH_3$)$_3$, —CH$(C_2H_5)_2$, —$C_2H_4$—CH($CH_3$)$_2$, —$C_6H_{13}$, —$C_3H_6$—CH$(CH_3)_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH$(CH_3)_2$, —CH($CH_3$)—CH($CH_3$)—$C_2H_5$, —$CH_2$—CH($CH_3$)—CH$(CH_3)_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —CH=$CH_2$, —$CH_2$—CH=$CH_2$, —C($CH_3$)=$CH_2$, —CH=CH—$CH_3$, —$C_2H_4$—CH=$CH_2$, —$C_7H_{15}$, —$C_8H_{17}$, —$CH_2$—CH=CH—$CH_3$, —CH=CH—$C_2H_5$, —$CH_2$—C($CH_3$)=$CH_2$, —CH($CH_3$)—CH=CH, —CH=C($CH_3$)$_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —$CH_2NH_2$, —$CH_2OH$, —$CH_2$—$CH_2NH_2$, —$C_6H_4$—$OCH_3$, —$C_6H_4$—OH, —$CH_2$—$CH_2$—$OCH_3$, —$CH_2$—$CH_2OH$, —$CH_2$—$OCH_3$, —$CH_2$—$C_6H_4$—$OCH_3$, —$CH_2$—$C_6H_4$—OH, n, m, r and s represent independently of each other an integer from 1 to 20;

p and q represent independently of each other an integer from 0 to 5.

The compounds of the general formula (I) are capable of evoking a very specific immune response in such a way that antibodies are produced in a host, which do not show any significant cross activities to other related compounds.

Further, the compounds of the general formula (I) are particular useful since these compounds are designed of being capable of binding to a carrier useful in vaccination, ensuring the correct orientation of the glycan in presence of free amine groups, which are characteristic to GPIs. The correct orientation of the glycan in presence of free amine is ensured by the substituent(s) $R^5$ and/or $R^6$ that present a terminal thiol group. The free terminal thiol group is more nucleophilic than the free amines under neutral or acid pH conditions, which are specific to the conjugation reaction, and therefore ensures natural orientation of the glycan on the carrier. This is a major advantage of using the terminal thiol group over, for instance, an amino or hydroxyl group.

Preferred substituents for R are: —H and

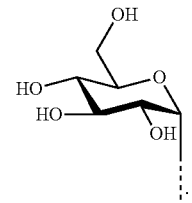

Preferred substituents $R^3$ are: —$NH_2$, —OH, and —$NHCOCH_3$.

Preferred substituents for $R^5$ and $R^6$ are: —$CH_2$—SH, —$C_2H_4$—SH, —$C_3H_6$—SH, —$C_4H_8$—SH, —$C_5H_{10}$—SH, —$C_6H_{12}$—SH, —$C_7H_{14}$—SH, —$C_8H_{16}$—SH, —$C_9H_{18}$—SH, —$C_{10}H_{20}$—SH, —CH=CH—SH, —C(=O)—$(CH_2)_n$—SH, more preferred —$C_6H_{10}$—SH, —$C_6H_{12}$—SH, and —$C_7H_{14}$—SH, and most preferred —$C_6H_{12}$—SH.

Further, in a preferred embodiment of the compounds of formula (I) according to the present invention R represents —H.

A further preferred embodiment of the present invention refers to compounds of formula (I) wherein R represents

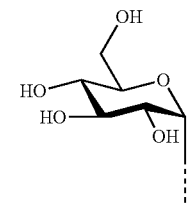

In another preferred embodiment of the compounds of formula (I) according to the present invention $R^1$ represents —OH. More preferred are compounds of general formula (I), wherein $R^1$ represents —OH and R represents —H.

In a particularly preferred embodiment of the compounds of formula (I) according to the present invention $R^2$ represents —OP(O)($OR^5$)($OR^6$), wherein $R^5$ represents —H, and $R^6$ represents —$C_6H_{12}$—SH.

Thus, especially preferred are compounds of the formula (II) and (III):
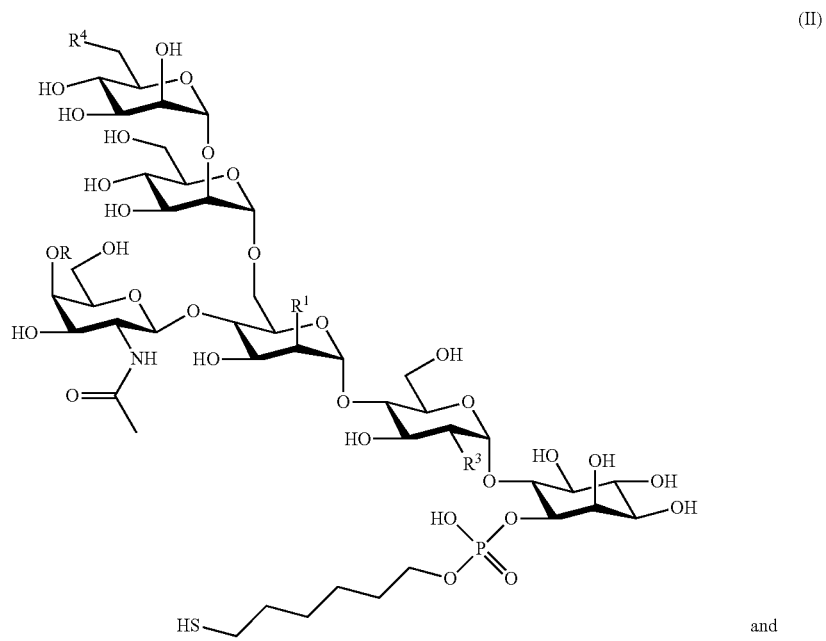
(II)
and
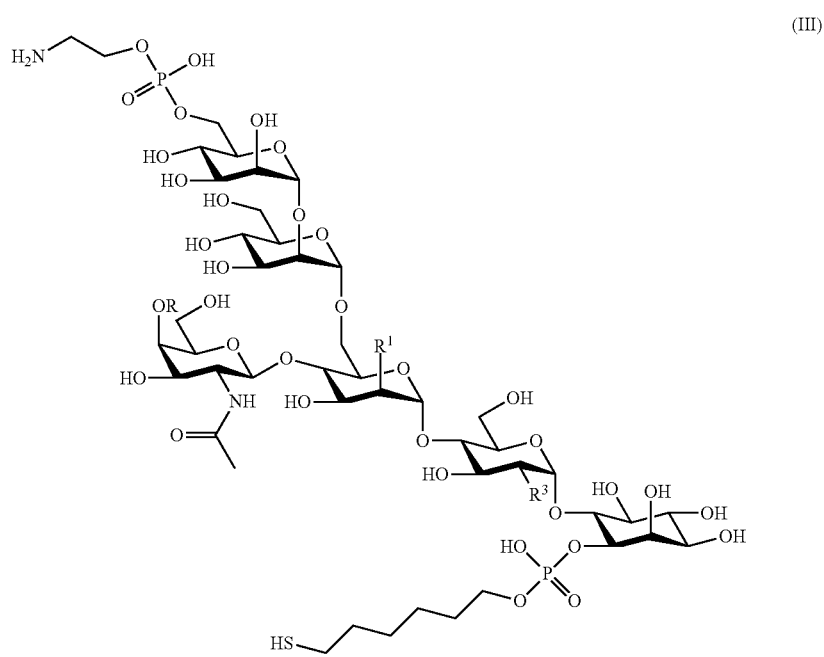
(III)

wherein the substituents R¹, R³ and R⁴ in (II) and R¹ and R³ in (III) have the meanings as defined herein.

In the formulae (II) and (III)

R represents preferably

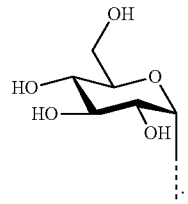

The compounds falling under general formula (I)-(III) are novel so that the present invention relates also to compounds of general formula (I)-(III), as well as stereoisomers, mixtures of enantiomers, mixtures of diastereomers, tautomers, hydrates, solvates and racemates and pharmaceutically acceptable salts of these compounds.

In yet another preferred embodiment of the present invention, the compound according to the general formula (I) is selected from the group comprising or consisting of:

6-O-(aminoethyl phosphono)-α-D-mannopyranosyl-(1→2)-α-D-mannopyranosyl-(1→6)-4-O-(α-D-glucopyranosyl-(1→4)-2-deoxy-2-acetamido-β-D-galactopyranosyl)-α-D-manno-pyranosyl-(1→4)-2-amino-2-deoxy-α-D-glucopyranosyl-(1→6)-1-O-(thiohexyl phosphono)-D-myo-inositol 6-O-(aminoethyl phosphono)-α-D-mannopyranosyl-(1→2)-α-D-mannopyranosyl-(1→6)-(2-O-(aminoethyl phosphono)-4-O-(α-D-glucopyranosyl-(1→4)-2-deoxy-2-acetamido-β-D-galactopyranosyl))-α-D-manno-pyranosyl-(1→4)-2-amino-2-deoxy-α-D-glucopyranosyl-(1→6)-1-O-(thiohexyl phosphono)-D-myo-inositol α-D-mannopyranosyl-(1→2)-α-D-mannopyranosyl-(1→6)-(2-O-(aminoethyl phosphono)-4-O-(α-D-glucopyranosyl-(1→4)-2-deoxy-2-acetamido-β-D-galactopyranosyl))-α-D-manno-pyranosyl-(1→4)-2-amino-2-deoxy-α-D-glucopyranosyl-(1→6)-1-O-(thiohexyl phosphono)-D-myo-inositol 6-O-(aminoethyl phosphono)-α-D-mannopyranosyl-(1→2)-α-D-mannopyranosyl-(1→6)-4-O-(2-deoxy-2-acetamido-β-D-galactopyranosyl)-α-D-manno-pyranosyl-(1→4)-2-amino-2-deoxy-α-D-glucopyranosyl-(1→6)-1-O-(thiohexyl phosphono)-D-myo-inositol 6-O-(aminoethyl phosphono)-α-D-mannopyranosyl-(1→2)-α-D-mannopyranosyl-(1→6)-(2-O-(aminoethyl phosphono)-4-O-(2-deoxy-2-acetamido-β-D-galactopyranosyl))-α-D-manno-pyranosyl-(1→4)-2-amino-2-deoxy-α-D-glucopyranosyl-(1→6)-1-O-(thiohexyl phosphono)-D-myo-inositol α-D-mannopyranosyl-(1→2)-α-D-mannopyranosyl-(1→6)-(2-O-(aminoethyl phosphono)-4-O-(2-deoxy-2-acetamido-β-D-galactopyranosyl))-α-D-mannopyranosyl-(1→4)-2-amino-2-deoxy-α-D-glucopyranosyl-(1→6)-1-O-(thiohexyl phosphono)-D-myo-inositol Another aspect of the present invention relates to a method for synthesis of a compound of formula (I) according to the following procedures:

a) providing a compound of the general formula (IV)

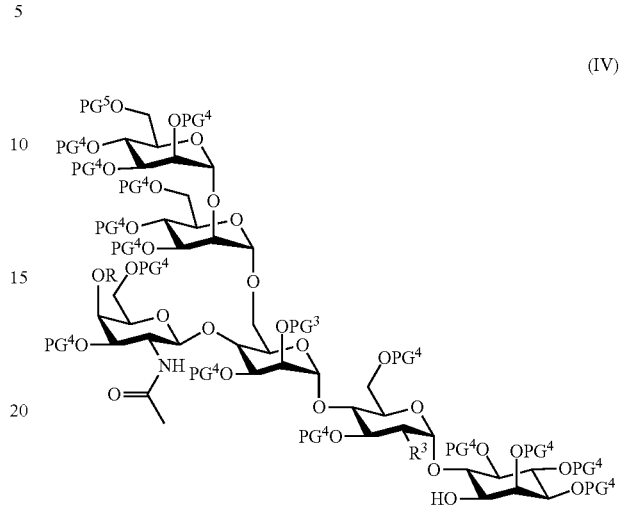

wherein

R represents —H, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, -Ph, —CH₂-Ph, or

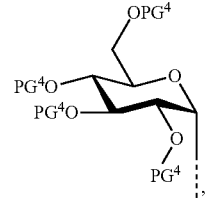

R³ represents —N₃, and

PG³ to PG⁵ represent suitable protecting groups for hydroxyl functional groups;

b) introducing the substituent R² by reacting a compound of step a) with an acid derivative selected from H—SO₂(OR⁵') or H—P(O)(OR⁵')(OR⁶') or a salt thereof, wherein R⁵' and R⁶' represent independently of each other —H, —CH₂—S—PG⁶, —C₂H₄—S—PG⁶, —C₃H₆—S—PG⁶, —C₄H₈—S—PG⁶, —C₆H₁₀—S—PG⁶, —C₆H₁₂—S—PG⁶, —C₇H₁₄—S—PG⁶, —C₈H₁₆—S—PG⁶, —C₉H₁₈—S—PG⁶, —C₁₀H₂₀—S—PG⁶, —CH=CH—S—PG⁶, —C(=O)—(CH₂)ₙ—S—PG⁶ and R⁵' and R⁶' are not simultaneously —H, wherein PG⁶ is a suitable protecting group for a thiol, c) introducing the substituent R⁴ by removing PG⁵ or by removing PG⁵ and subsequent conversion with an acid of the formula H—P(O)(OH)—O—C₂H₄—NH(PG⁷) or a salt thereof, wherein PG⁷ is a suitable protecting group for an amine;

d) introducing the substituent R¹ by removing PG³ or by removing PG³ and subsequent conversion with an acid of the formula H—P(O)(OH)—O—C$_2$H$_4$—NH(PG$^7$) or a salt thereof, wherein PG$^7$ is a suitable protecting group for an amine;

e) deprotecting the compound of step d) by removing the protection groups PG$^4$, PG$^6$ and PG$^7$ resulting in a compound of formula (I)

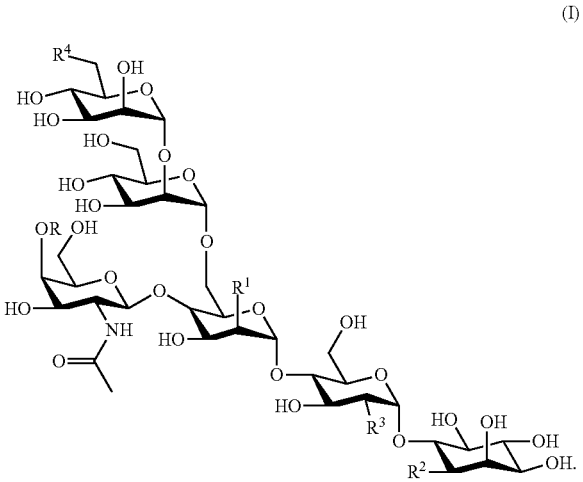

(I)

wherein R, R$^1$-R$^4$ have the meanings as defined herein, and wherein the steps c) and d) can be performed consecutively in the row c) and then d) or d) first and then c) thereafter or simultaneously.

The protecting groups PG$^3$, PG$^4$, PG$^5$, PG$^6$ and PG$^7$ are commonly used protecting groups in organic synthesis, preferably for amines, hydroxyl groups, thiols, imines, carbonyls or other common functional groups.

More specifically, PG$^3$, PG$^4$ and PG$^5$ preferably are suitable protecting groups for hydroxyl groups, more preferably different suitable protecting groups for hydroxyl groups capable of being removed subsequently one after another by a suitable sequence of deprotection reactions. Preferred protection groups for hydroxyl groups are benzyl, benzoyl, 4-O-p-methoxybenzyl, allyl, acetyl, methylsulfonylethoxycarbonyl, levulinyl, dimethoxytrityl, 2-naphthylmethyl, triisopropylsilyl, tert-butyldimethylsilyl, tert-butyldiphenylsilyl, 2-trim ethyl-silylethoxymethyl. More specifically, in a preferred embodiment of the present invention protecting group PG$^3$ may be levulinyl, protecting group PG$^4$ may be benzyl and protecting group PG$^5$ may be triisopropylsilyl.

Preferred protecting groups for amines form carbamates such as tert-butyloxy carbonyl, 9-fluorenylmethyl carbonyl, allyl carbonyl, trichloroethyl carbonyl, benzylcarboxy carbonyl; or form amides such as acetyl or trichloro acetyl. In a preferred embodiment of the present invention protecting group PG$^7$ is a benzylcarboxy carbonyl group.

Also, protecting groups for hydroxyl groups may serve as well as protecting groups for thiols. Therefore, preferred protecting groups for thiols groups are benzyl, benzoyl, 4-O-p-methoxybenzyl, allyl, acetyl, methylsulfonylethoxycarbonyl, levulinyl, dimethoxytrityl, 2-naphthylmethyl, triisopropylsilyl, tert-butyldimethylsilyl, tert-butyldiphenylsilyl, 2-trimethylsilylethoxymethyl. Specifically, in a preferred embodiment of the present invention protecting group PG$^6$ is a benzyl group.

According to the present invention steps c) and d) are not supposed of being strictly performed in the order that step c) is accomplished before step d) is performed. Therefore, in one embodiment of the present invention step c) is performed before step d). In another embodiment of the present invention step d) is first performed and afterwards step c) is conducted. Thus, step c) is performed after step d). Therefore, these are two options wherein steps c) and step d) are performed consecutively. However, in another preferred embodiment of the present invention step c) and step d) are performed simultaneously. In such embodiment protection groups PG$^3$ and PG$^5$ are removed together and then optionally, substituents R$^1$ and R$^4$ being H—P(O)(OH)—O—C$_2$H$_4$—NH(PG$^7$) or a salt thereof with PG$^7$ having the meaning as defined herein, are introduced at the same time.

In case the compounds of the present invention bear basic and/or acidic substituents, they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Further, it is also possible that the compounds of the present invention bear simultaneously basic and acid groups. Further, it may also occur that these basic and acid groups appear to be in close vicinity to one another enabling an intramolecular proton transfer from the acidic group the basic group. Therefore, in a preferred embodiment of the present invention the compound of the formula (I) may be zwitter-ionic, bearing at least e.g. one —O$^-$ and one —NH$_3^+$ group.

Some of the compounds of the present invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

The possibility of a synthesis of the compounds according to formula (I) enables production of sufficient and pure amounts of the desired GPI structure, which may support research towards understanding of the pathomechanism of *T. gondii* infection and enables designing a vaccine against *T. gondii*.

Surprisingly it was found that the compounds of general formula (I) are suitable to raise an immune response in an animal, and are suitable for vaccination against infectious diseases. Therefore, another aspect of the present invention relates to the use of a compound of general formula (I) for vaccination against toxoplasmosis. One embodiment of the invention is further a compound of the general formula (I) for vaccination against an infection with *T. gondii*. The invention relates also to the use of a compound of general formula (I) for the manufacture of a vaccine against toxoplasmosis.

Further was found that extraordinary potent and stable vaccine can be derived when a compound of general formula (I) is covalently linked to a carrier through the terminal thiol group, preferably as thio ether or thio ester. Saccharides are known by the person skilled in the art as TI-2 (T cell independent-2) antigens and poor immunogens. Therefore, to produce a saccharide-based vaccine, said saccharides are linked or conjugated to a "carrier" to provide a conjugate, which presents an increased immunogenicity in comparison with the saccharide. Thus, a compound of general formula (I) is linked to a carrier through the terminal thiol group to provide a conjugate consisting on the compound of general formula (I) covalently linked to a carrier.

The immune response raised against the conjugate consisting of compound 3 covalently linked to $CRM_{197}$ clearly recognized the parasite (see FIG. 4, immunofluorescence picture). Analysis of the polyclonal antibodies revealed that the immune response against the conjugate was very specific. The serum antibodies bound compound 3, but did not show cross reactivity to the structurally close related compound 5, which is a mammalian structure (see FIG. 3). It is important to note that compound 3 does not induce cross-reactivity to human structures, which excludes the possibility of raising an autoimmune response.

The immune response raised against the conjugate consisting of compound 4 covalently linked to $CRM_{197}$ clearly recognized the parasite and located the GPI at the apical end of the parasitic cell (see FIG. 13, immunofluorescence picture). These findings are very important because the apical complex of *T. gondii* is used for invading host cells. Induction of an immune response against this site of the parasite is capable of blocking the invasion mechanism of *T. gondii*. Together with the opsonizing properties of the raised antibodies, this vaccine can be capable of inducing immunity against this parasite. Analysis of the polyclonal antibodies revealed that the immune response against the conjugate was very specific. The serum antibodies bound compound 4, but did not show cross reactivity to substructures of this GPI carbohydrate (see FIG. 12).

The specific immune response both conjugates elicited show that only compounds 3 and 4, presenting the full glycan structure, are able to induce the production of antibodies in vivo that are able to recognize the parasite *T. gondii*. Although WO 1997010249 A1 shows that substructures of GPI carbohydrate covalently attached to a carrier are sufficient to raise an immune response that recognizes the parasite *T. gondii*, our results indicate that these substructures of compound 4 (see FIG. 12; one trisaccharide and two pentasaccharides with a varying degree of phosphorylation) seem not be sufficient, because they are not recognized by the polyclonal antibody response.

The present invention relates therefore to a compound of general formula (I) covalently linked to a carrier. Particularly preferred is that said carrier is a peptidic compound and even more preferred a bacterial peptide or a compound derived from a bacterial peptide. In another preferred embodiment, said carrier is a glycosphingolipid with immunomodulatory properties.

As used herein, a carrier is a pharmacological or immunological agent that modifies the effect of other agents, such as an active agent or vaccine. The term "carrier" as used herein refers to a compound used as a carrier protein, to which a compound of general formula (I) is linked and which enhances the recipient's immune response to the compound of general formula (I). In a preferred embodiment, the term "carrier" as used herein refers to a glycosphingolipid with immunomodulatory properties, to which a compound a compound of general formula (I) is linked and which enhances the recipient's immune response to the compound of general formula (I).

It is preferred that the carrier to which the compound of general formula (I) is covalently linked is a carrier protein. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH) or cholera toxoid (CT).

It is particularly preferred that the carrier to which the compound of general formula (I) is covalently linked, is selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid or a mutated tetanus toxoid. The term "toxoid" as used herein refers to a bacterial toxin (usually an exotoxin) whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. A modified toxoid, as used herein, is a bacterial toxoid, on which a functional group X has been introduced by reacting said bacterial toxoid with a bifunctional linker. Thus, the modified toxoid presents a or is modified with functional group X, said functional group X being capable of reacting with the terminal thiol group of the compounds of general formula (I). The term "bifunctional linker" refers to a bifunctional molecule containing functional group X and functional group Y, wherein functional group X is capable of reacting with the terminal thiol group on the compounds of general formula (I) and the functional group Y is capable of reacting with a carrier. It is especially preferred that the compound of general formula (I) is covalently linked to the non-toxic mutated diphtheria toxin $CRM_{197}$, which is modified with the functional group X. Preferably, the compound of general formula (I) is covalently linked to the non-toxic mutated diphtheria toxin $CRM_{197}$, which is modified with maleimide. In the most preferred embodiment, the compound of general formula (I) is covalently linked to the non-toxic mutated diphtheria toxin $CRM_{197}$, which is modified with α-iodoacetamide.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is used as a carrier protein in a number of approved conjugate vaccines, such as the pneumococcal vaccine Prevnar 13® (Pfizer Inc.).

In one aspect of the present invention the compounds of the formula (I) are covalently linked to a carrier for the use in a vaccine. The binding or covalent linkage to the carrier can be accomplished by first providing a suitable carrier capable of stimulating the immune system's response to a target antigen, but does not in itself confer immunity as defined above. Examples of suitable carriers include, but they are not restricted to peptidic compounds, bacterial peptides, compounds derived from a bacterial peptides, mutated toxoids and glycosphingolipids with immunomodulatory properties.

In a preferred embodiment of the present invention such a suitable carrier may be $CRM_{197}$. Said suitable carriers are able to react with the functional group Y of the bifunctional linker to provide a carrier modified with a functional group X. In a preferred embodiment of the present invention the carrier is modified by at least one functional group X of the group comprising or consisting of maleimide; α-iodoacetyl; α-bromoacetyl; N-hydroxysuccinimide ester (NHS), 2-pyridyldithiols, thiol and vinyl (see also FIG. 5A). The introduction of such functional group X on the carrier is preferably accomplished by reaction of a suitable carrier with a bifunctional linker that bears on one side the functional group Y prone of reacting with the suitable carrier and on the other side a functional group X prone to react with the terminal thiol group of the compounds of general formula (I).

In a preferred embodiment of the present invention such a bifunctional linker bears on one side a vinyl functional group X prone to react with the terminal thiol group of the compound of general formula (I), and on the other side a N-hydroxysuccinimide ester functional group Y that is prone of reacting with lysine side amino group of a peptidic compound.

In another preferred embodiment of the present invention such a bifunctional linker bears on one side a maleimide functional group X prone to react with the terminal thiol group of the compound of general formula (I), and on the other side a N-hydroxysuccinimide ester functional group Y that is prone of reacting with lysine side amino group of a peptidic compound.

Preferably, such a bifunctional linker bears on one side an α-iodoacetyl functional group X prone to react with the terminal thiol group of the compound of general formula (I), and on the other side a N-hydroxysuccinimide ester functional group Y that is prone of reacting with lysine side amino group of a peptidic compound.

In another embodiment, said carrier is preferably a glycosphingolipid with immunomodulatory properties, and more preferably (2S,3S,4R)-1-(α-D-galactopyranosyl)-2-hexacosanoylaminooctadecane-3,4-diol.

The term glycosphingolipid with immunomodulatory properties, as used herein, refers to a suitable glycosphingolipid capable of stimulating the immune system's response to a target antigen, but which does not in itself confer immunity as defined above.

Glycoshingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or poly-substituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci.* USA, 1998, 95, 5690).

The conjugates of the compounds of general formula (I) to the glycosphingolipid with immunomodulatory properties have the advantage of being heat stable. To be suitable for covalent linkage to the compounds of general formula (I), on the glycosphingolipid with immunomodulatory properties a functional group X is introduced by reacting the glycosphingolipid with immunomodulatory properties with a bifunctional linker. Thus, a modified glycosphingolipid with immunomodulatory properties presents or is modified with a functional group X prone to react with the terminal thiol group of the compounds of general formula (I) preferably by formation of a covalent bond. Preferably, the glycosphingolipid with immunomodulatory properties is modified at the C6 of the carbohydrate moiety. In a preferred embodiment of the present invention the carrier is modified by at least one functional group X of the group comprising or consisting of maleimide, α-iodoacetyl, α-bromoacetyl, N-hydroxysuccinimide ester (NHS), 2-pyridyldithiols, thiol and vinyl (see also FIG. 5A). The introduction of such functional group X on the glycosphingolipid with immunomodulatory properties is preferably accomplished by reaction of a suitable glycosphingolipid with immunomodulatory properties with a bifunctional linker that bears on one side a functional group X prone of reacting with the terminal thiol group of the compound of general formula (I) and on the other side a functional group Y that is prone to react with the glycosphingolipid with immunomodulatory properties.

In a preferred embodiment of the present invention such a bifunctional linker bears on one side α-iodoacetyl functional group X prone to react with the terminal thiol group of a compound of general formula (I), and on the other side a N-hydroxysuccinimide ester functional group Y that is prone of reacting with an amino group of a glycosphingolipid with immunomodulatory properties.

In another preferred embodiment of the present invention such a bifunctional linker bears on one side maleimide functional group X prone to react with the terminal thiol group of a compound of general formula (I), and on the other side a N-hydroxy succinimide ester functional group Y that is prone of reacting with an amino group of a glycosphingolipid with immunomodulatory properties.

Preferably, such a bifunctional linker bears on one side vinyl functional group X prone to react with the terminal thiol group of a compound of general formula (I), and on the other side N-hydroxysuccinimide ester functional group Y that is prone of reacting with an amino group of a glycosphingolipid with immunomodulatory properties.

For the preferred embodiment wherein the carrier is modified with a vinyl functional group X, a compound of the formula (I) can be covalently linked to the vinyl functional group X by a thiol-ene reaction by means of irradiation with UV light and/or in the presence of an initiator to form a stable thioether bond (see also FIG. 5*b*).

For the preferred embodiment wherein the carrier is modified with a maleimide functional group X, the terminal thiol group of a compound of general formula (I) adds via a Michael addition to the maleimide moiety.

For the preferred embodiment wherein the carrier is modified with a α-iodoacetamide functional group X, the terminal thiol group of a compound of the formula (I) substitutes the iodide of the α-iodo-acetyl moiety.

Further, in the preferred embodiments wherein the carrier is a protein carrier, these functionalization reactions are performed in such a way that more than one functional group X is introduced on the carrier. Thus, the said protein carrier presents or is modified with more than one functional group X. However, it is also possible that just one functional group X is introduced on the carrier. In a preferred embodiment of the present invention the number of functional groups X introduced on the carrier after the functionalization reaction ranges preferably from 5 to 100, more preferably from 10 to 50, and most preferably from 10 to 40. After the carrier was modified with functional group X by one said functionalization reactions, the compounds of the present invention are added in order to bind the terminal thiol group, e.g. to the maleimide double bond by an addition-like reaction. Therein, it is possible to adjust the number of molecule of the formula (I) being linked to the carrier. The number of molecules of the formulas (I) being linked to the carrier can range preferably from 1 to 100, more preferably from 3 to 50, and most preferably from 5 to 15. In a preferred embodiment the number of molecules of the formulas (I) being linked to a carrier ranges from 1 to 15, more preferably from 2 to 10 and especially preferred from 3 to 7.

Another aspect of the present invention relates to the use of the compound of general formula (I) covalently linked to a carrier for vaccination against toxoplasmosis. One embodiment of the invention is further a compound of the general formula (I) covalently linked to a carrier for vaccination against an infection with *T. gondii*. The invention relates also to the use of a compound of general formula (I) covalently linked to a carrier for the manufacture of a vaccine against toxoplasmosis.

The examples of the present invention show that the compounds of general formula (I) linked to a carrier elicited a highly specific antibody response to the compounds of general formula (I) in mice, including isotype switching and affinity maturation (see example 14 and example 15). Moreover, the generated antibodies recognized the natural GPI on the parasite (see example 16).

Another aspect of the present invention relates to pharmaceutical formulations and pharmaceutical compositions for vaccination containing a compound of general formula (I) optionally covalently linked to a carrier as an active ingredient, together with at least one pharmaceutically acceptable carrier, excipient, solvent and/or diluents.

Further preferred, the pharmaceutical composition is formulated in the form of a lyophilisate or liquid buffer solution.

The compound of general formula (I) optionally covalently linked to a carrier can also be administered in form of its pharmaceutically active salt optionally using substantially nontoxic pharmaceutically acceptable carrier, excipients, adjuvants or diluents. The pharmaceutical composition, which is used as a vaccine is prepared in a conventional solid or liquid carrier or diluents and may comprise a conventional pharmaceutically acceptable adjuvant at suitable dosage level in a known way. Classically recognized examples of conventional pharmaceutically acceptable adjuvants include oil emulsions (e.g., Freund's adjuvant), saponins, aluminium or calcium salts (e.g., alum), non-ionic block polymer surfactants, and many others.

The inventive pharmaceutical composition may be administered by any appropriate means, including but not limited to inhalation, injection (intravenous, intraperitoneal, intramuscular, subcutaneous) by absorption through epithelial or mucocutaneous linings (oral mucosa, rectal and vaginal epithelial linings, nasopharyngial mucosa, intestinal mucosa); orally, rectally, transdermally, topically, intradermally, intragastrically, intracutaneously, intravaginally, intravasally, intranasally, intrabuccally, percutaneously, sublingually, or any other means available within the pharmaceutical arts. The compounds of the invention of the general formula (I) are present in said vaccine formulation in the range of 10 to 1000 µg/g.

It was shown that the GPI of *T. gondii* containing the additional α-Glc in the side chain is identical with the known "low molecular weight antigen" of this parasite and IgM antibodies against this structure could be detected in sera from patients with toxoplasmosis (*J. Biol. Chem.* 1992, 267, 11721.). The current ELISA-based diagnostic techniques in order to identify acute toxoplasmosis have a high rate of false-positive results because high IgM responses can be detected even more than a year after a primary infection. Moreover, so far isolates of the parasite are used as antigens for the test, and therefore their quality of production can vary extremely. In literature it has been shown that other glycolipids are included in these isolates, which is one of the reasons for false-positive results (*J. Clin. Microbiol. Infect. Dis.* 2003, 22, 418). Disadvantages of overtreatment of healthy and infected patients, especially pregnant women, who would require a stressful diagnosis and need medical treatment including pyrimethamine, sulfadiazine, and folinic acid (PSF) after 18 weeks of gestation, which are partially inhibitors of the enzyme dihydrofolate reductase and cause severe side effects such as cardiac arrhythmias and leukopenia, are obvious. Furthermore inhibition of the dihydrofolate reductase can lead to congenital malformations, including neural tube defects, which are of course harmful for the unborn child (*PLoS Negl Trop Dis.* 2011; 5(9), 1333). A test based on a single synthetic antigen is therefore a clear advantage over the commercially available diagnostic tools.

Moreover the inventors could show that the compounds according to formula (I) can be used in immunological assays for diagnosis of diseases caused by *T. gondii*. Such assays comprise, for instance, microarray and ELISA useful for diagnosis of diseases caused by *T. gondii*. Therefore another aspect of the present invention refers to the use of a compound of formula (I) for diagnosis of toxoplasmosis. Thus, especially preferred embodiments of the present invention relate to pure synthetic compounds of formula (I) for diagnosis of toxoplasmosis.

It is preferred that the compound of formula (I) is used for diagnosis of acute toxoplasmosis. Acute toxoplasmosis is characterized by a high-titer of IgM in the serum of the patients and the fact that IgG is not present or only with a low-titer. It is preferred that the compound of formula (I) is used for the differential diagnosis of acute toxoplasmosis, that means that the compound of formula (I) is used in a diagnostic test which allows not only to determine if a patient is infected with *T. gondii*, but also to differentiate between an acute infection and a latent or chronic infection.

Thus, one especially preferred embodiment of the present invention relates to the use of only one specific defined compound of formula (I) for diagnosis of toxoplasmosis. It is further preferred that the compound of formula (I) used for diagnosis of toxoplasmosis is substantially pure, having a purity of 95%, preferably 96%, more preferably 97%, still more preferably 98%, and most preferably 99%. In addition, the chemically synthesized compound of formula (I) does not have any microheterogenicity as the oligosaccharides from biological sources do. Nevertheless, the use of a mixture of different compounds of formula (I) for diagnosis of toxoplasmosis is possible, but is less preferred.

There are different possibilities for the choice of an assay system in which a compound of formula (I) is used for diagnosis of toxoplasmosis. An assay conducted for diagnostic purposes according to the invention may be an immune assay like a solid-phase enzyme immunoassay (EIA), an enzyme linked immunosorbent assay (ELISA), especially an "indirect" ELISA, a radioimmune assay (RIA) or a fluorescence polarization immunoassay. For the use of a compound of formula (I) in such assays it could be necessary to immobilize the compound of formula (I) on a carrier material, preferably a solid carrier material.

Therefore a compound of formula (I) may be immobilized on a carrier material, particularly for diagnostic applications. One preferred embodiment of the present invention is a compound of general formula (I) immobilized on a carrier material by covalent bonding. One particularly preferred embodiment of the present invention is a compound of general formula (I) immobilized on a carrier material by direct or indirect covalent bonding. Thereby direct covalent bonding is especially preferred.

There are also carrier materials commercially available made from polymers with reactive functional introduced for covalent bonding. One example are microplates named CovaLink™ NH by Thermo scientific, which allow covalent binding through a secondary amine group.

In a preferred embodiment the solid carrier material is selected from the group comprising or consisting of: glass slides, microtitre plates, test tubes, microspheres, nanoparticles or beads.

It is particularly preferred that the carrier material is a glass slide or a microtitre plate. A microtitre plate or microplate or microwell plate, is a flat plate with multiple "wells" used as small test tubes. Typically a microtitre plate having 6, 24, 96, 384 or even 1536 sample wells can be used. Microplates are produced from many different materials, like polycarbonate for microtitre plate used for PCR. The most common is polystyrene as used for most optical detection microplates. It can be colored white by the addition of titanium dioxide for optical absorbance or luminescence detection or black by the addition of carbon for fluorescent biological assays.

"Direct covalent bonding" as used herein refers to immobilization of a compound of general formula (I) by reacting a functional group of the compound of general formula (I) with a functional group of the material the carrier material is made from. It is preferred that the functional group of the compound of general formula (I) is $R^2$ as defined above. Possible reactive, functional groups of the carrier material may be: thiols, carbonyls, carboxyls, vinyls, halides such as fluorides, chlorides, bromides and iodides, maleimides, succinimide esters.

"Indirect covalent bonding" as used herein refers to immobilization of a compound of general formula (I) on a carrier material, wherein the compound of general formula (I) is covalently linked to a second compound, which mediates the immobilization to the carrier material. It is preferred that this second compound is a protein, which does not cause an immune reaction. It is important that the second compound itself is most probably not bound by any antibody present in the blood or serum of a patient to avoid false positive results. Further the second compound should be able to be immobilized on the carrier material, by covalent or non-covalent bonding. It is preferred that this second compound is selected from the group comprising or consisting of bovine serum albumin (BSA), human serum albumin (HAS), gelatin or casein. The immobilization using indirect covalent bonding therefore refers preferably to covalent bonding of a compound of general formula (I) to a protein as a second compound (e.g. using the free amino groups of a protein) and subsequently binding of the protein to the carrier material by covalent bonding or non covalent interaction between the carrier material and the protein.

Possible non-covalent interactions are: hydrogen bonds, ionic bonds, van der Waals forces, and hydrophobic interactions. Many polymers, such as polystyrene and polypropylene are hydrophobic in nature. Nevertheless there are also manufacturers, which supply carrier materials having specialized surfaces optimized for different adhesion conditions.

However, immobilization, especially using indirect covalent bonding, may also occur by strong adhesion. Thus, an effective immobilization according to the present invention may be realized not only by chemical bonding, but also unbound by immobilization related to physisorption. As key feature for physisorption acts the phenomenon that the force for adhesion is caused by van der Waals force. The term "unbonded" refers to a bonding other than covalent bonding.

Chemisorption as immobilization form according to the present invention uses chemical bonds between the carrier material and a compound of formula (I). Such bond may be covalent, but may also be ionic. Compounds of the general formula (I) can therefore be covalently attached via chemisorption to for example gold or silver nanoparticles as well as surfaces consisting of those noble metals and CdSe quantum dots.

In a preferred embodiment of the present invention immobilization of a compound of the formula (I) on a carrier material is realized by direct covalent bonding namely a chemical reaction between these two reactants, preferably by a substitution reaction. In a more preferred embodiment of the present invention the carrier material is modified with a functional group, which is capable of leaving the carrier material upon reaction with the compound of the present invention. Such functional group may be bound directly to a composing molecule of the carrier material or may be bound to a linker, which is directly bound to the composing molecule of the carrier material. Thus, in a more preferred embodiment of the present invention the carrier material is modified to bear a suitable leaving group. Suitable leaving groups may be halides such as chlorides, bromides and iodides, succinimide esters, and esters. Such leaving groups may be or may be incorporated in maleimide, α-iodoacetyl, α-bromoacetyl, N-hydroxysuccinimide ester (NHS) and 2-pyridyldithiols. In yet more preferred embodiment, the leaving group on the carrier material is capable to preferably react with thiols, preferably upon proton exchange. In a preferred embodiment of the present invention the carrier material is functionalized with a succinimidyl hydroxide functional group, more preferably N-succinimidyl hydroxide, which will leave the carrier material upon reaction with a compound of the present invention as N-hydroxysuccinimide.

Modification of the carrier material by introduction of a suitable leaving group is preferably carried out by reaction of an unmodified carrier material with a reactive bifunctional molecule A, preferably a bifunctional molecule with a molecular bridge or spacer arm between the two functional groups: a functional group A1 prone to react with the carrier material and a functional group A2, which is a suitable leaving group. In a preferred embodiment of the present invention functional groups A1 willingly reacting with the carrier material comprises sulfosuccinimide esters and succinimides. One further preferred aspect of the bifunctional molecules A is the ability of providing the functional group meant to bind with a compound of the formula (I) is an appropriate distance to the carrier material. Such an appropriate distance is provided by a molecular bridge or spacer arm of suitable length. Such a molecular bridge or spacer arm may have a length preferably from 3 Å ($10^{-10}$ m) to 10 nm, more preferably from 5 Å to 50 Å, and most preferably from 6 Å to 30 Å. Suitable reactive bifunctional molecules for modification of the carrier material comprise succinimidyl (4-iodoacetyl) am inobenzoate (sulfo-SIAB), succinimidyl-3-(bromoacetamido)propionate (SBAP), disuccinim idyl glutarat (DSG), 2-pyridyldithiol-tetraoxatetradecane-N-hydroxysuccinimide (PEG-4-SPDP) (see FIG. 7).

In a preferred embodiment the assay conducted for diagnostic purposes according to the invention is a fluorescence polarization assay. For such assay, the compound of general formula (I) is immobilized on a fluorescent carrier material. The compound of general formula (I) covalently bound to a fluorescent carrier material could be used for detection of antibodies in human sera specific to the compounds or general formula (I) by fluorescence polarization. Fluorescence polarization is a known powerful method for the rapid and homogeneous analysis of molecular interactions in biological and chemical systems. The principles of fluorescence polarization are based on the excitation of a fluorescent molecule with polarized light. This results in the emission of photons in the plane, which is parallel and perpendicular to the excitation plane and yields information about the local environment of the fluorescent molecule. The rotation of fluorescent molecule in solution can be observed by measuring the rotation of the plane of polarization of the light that was originally beamed in. The observed rotation depends on the rotation relaxation time and is only influenced by the temperature, the viscosity and the molecular weight of the fluorescent molecule. Thus, fluorescence polarization is a suitable method for measuring these parameters and in particular changes in these parameters. The term "fluorescent carrier material" as used herein refers to a compound that absorbs light energy of a specific wavelength and re-emits light at a longer wavelength. In a preferred embodiment, the fluorescent carrier material is fluorescein isothiocyanate (FITC), which has an excitation/emission peak at 495/517 nm and can be coupled to the compounds of general formula (I) through the isothiocyanate group.

Another aspect of the present invention is the use of a compound of general formula (I) immobilized on a carrier material by covalent bonding for diagnosis of toxoplasmosis. The diagnosis of acute toxoplasmosis is preferred.

One embodiment of the present invention relates to a kit comprising at least one compound of general formula (I) immobilized on a carrier material by covalent bonding or the compound of general formula (I) for immobilization on a carrier.

A kit in molecular biology or in medical diagnostics is a package, which includes all necessary ingredients for performing a certain method or singular step. Standard chemicals as present in any standard molecular biology or medical laboratory are normally not included. Nevertheless, some of these standard chemicals may be indispensable to carry out the diagnosis or the immobilization properly. It is understood that all ingredients are provided in quantities that allow for a proper execution of the desired reactions for the majority of scientific, diagnostic and industrial applications.

Often, but not always, these ingredients are provided in already prepared solutions ready- or close to ready-for-use. There may be also combinations of different ingredients already added together. A further advantage is that such kits use to be verified. Therefore the operator doesn't have to prove again the viability of the diagnostic method and can save on at least some control experiments.

Such a kit according to the invention shall include at least the following components:

A) compound of general formula (I) immobilized on a carrier material by covalent bonding
B) at least one antibody, like detection antibody
C) a standard solution The following components may also be included in such kits:

D) blocking solution
E) wash solution
F) sample buffer

An antibody in the kit may be a specific antibody, which can be used as a capture antibody. But preferably it is at least an enzyme-linked secondary antibody used as detection antibody that binds specifically to antibody's Fc region. For quantitative determinations, the optical density (OD) or fluorescence of the sample is compared to a standard curve, which is typically a serial dilution of a known-concentration solution of the target molecule (a standard solution). A blocking solution may be a solution of a non-reacting protein, such as bovine serum albumin or casein, which is added to block any plastic surface in the well that remains uncoated by the antigen. Washing solutions are used to remove unbound components. A sample buffer may be used to dilute the sample of the patient (blood, serum, urine) so that the concentration of the target molecule is in the range which can normally be detected by the test system used.

If the kit shall be allow for the immobilization of a compound of general formula (I) on a solid carrier material the kit should include at least:

A) A compound of general formula (I)
B) A carrier material, like a microtiter plate Thereby the carrier material may be modified, for example the carrier material may be modified with a functional group as described above.

The following components may also be included in such kits:

C) blocking solution
D) wash solution
E) reaction buffer

EXPERIMENTAL PART

Figure 1:
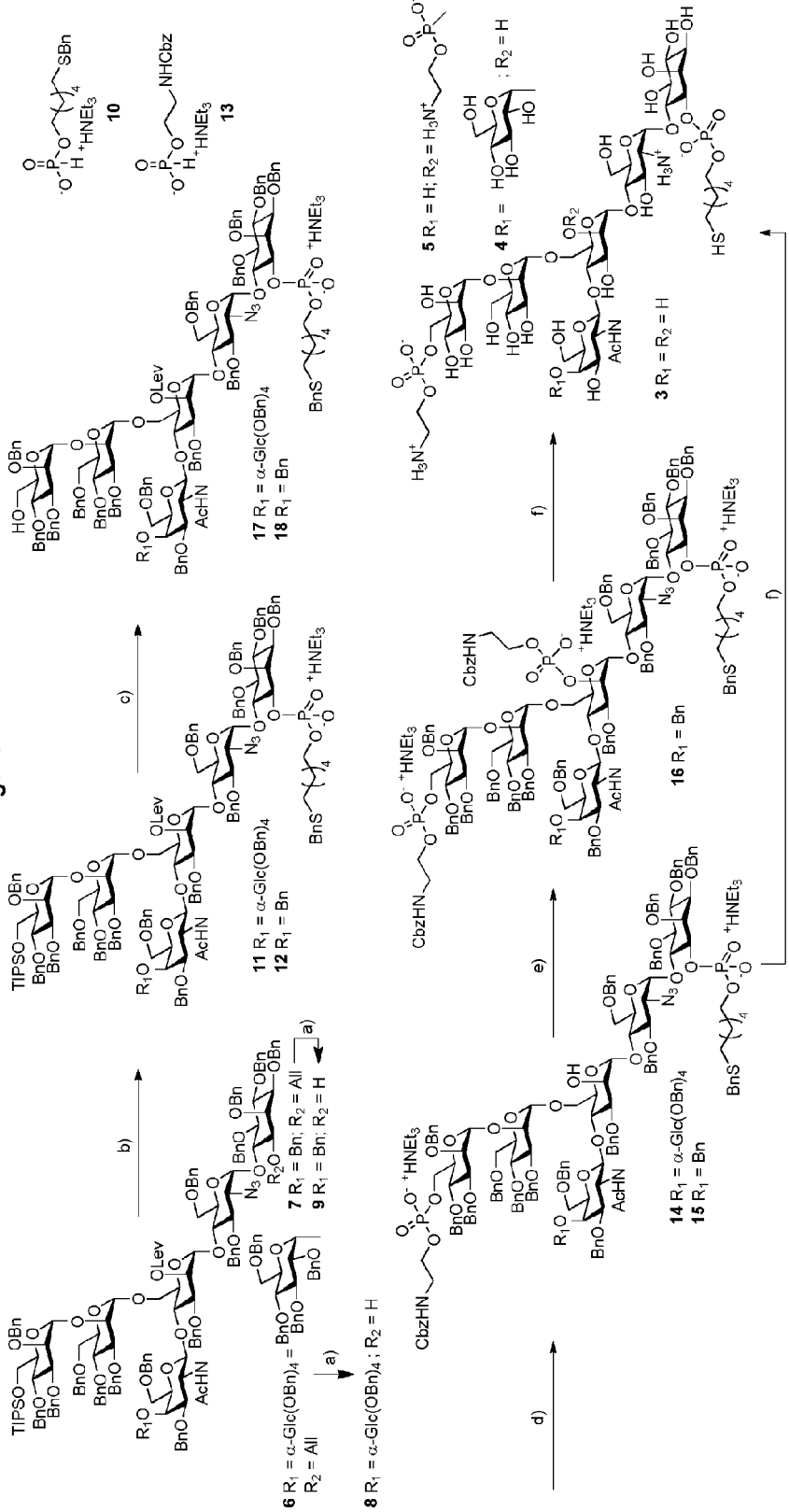
FIG. 1: Reaction scheme for the preparation of glycans 3, 4 and 5 as examples for a phosphate linked GPI.

Part A1: Preparation of Phosphate Linked Thiol Functionalized GPI

Example 1: Triethylammonium 2,3,4-Tri-O-benzyl-6-O-triisopropylsilyl-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-2-O-levulinyl-α-D-mannopyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (Compound 12)

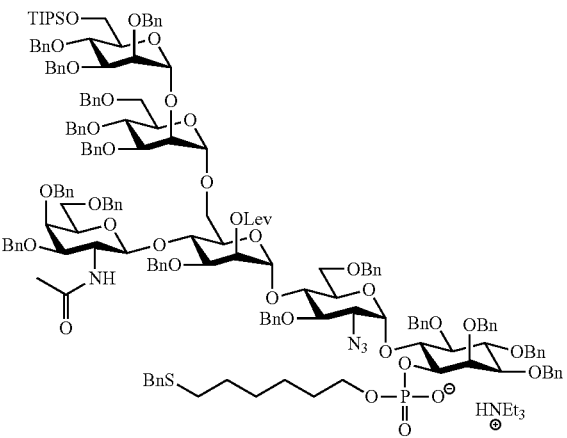

2,3,4-Tri-O-benzyl-6-O-triisopropylsilyl-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-2-O-levulinyl-α-D-mannopyranosyl-(1→4)-2-azido-3,6-di-O-benzyl-2-deoxy-α-D-glucopyranosyl-(1→6)-1-O-allyl-2,3,4,5-tetra-O-benzyl-D-myo-inositol (compound 9) (20 mg, 7.26 μmol, 1 equiv) and triethylammonium 6-(benzylthio)hexyl phosphonate (compound 10) (12.7 mg, 33 μmol, 4.5 equiv) are co-evaporated 3 times with 2 mL dry pyridine. The residue is dissolved in 2 mL dry pyridine and PivCl (6.70 μL, 54 μmol, 7.5 equiv) is added. The solution is stirred for 2 h at r.t. before water (10 μL, 0.56 mmol, 76 equiv) and iodine (10.1 mg, 40 μmol, 5.5 equiv) are added. The red solution is stirred for 1 h and is quenched with sat. $Na_2S_3O_3$. The reaction mixture is diluted with 10 mL CHCl3 and dried over $Na_2SO_4$. The solvents are removed in vacuo and the residue is purified through flash column chromatography (starting from CHCl3/MeOH 0%→5% MeOH) to yield yellow oil (18 mg, 5.9 μmol, 82%).

$[α]_D^{20}$=+32.6 (c=1.00 in $CHCl_3$); $v_{max}$ (neat) 2926, 2864, 2107, 1742, 1720, 1677, 1454, 1098, 1059, 1028 $cm^{-1}$; $^1$H NMR (600 MHz, $CDCl_3$) δ 7.35 (d, J=7.4 Hz, 2H), 7.31-7.04 (m, 81H), 6.99 (dd, J=6.6, 2.8 Hz, 2H), 5.94 (d, J=8.8 Hz, 1H, NH), 5.86 (d, J=3.7 Hz, 1H, $GlcNH_2$-1), 5.27-5.24 (m, 2H, ManI-2), 5.09 (d, J=1.2 Hz, 1H), 4.96 (d, J=12.0 Hz, 1H, $CH_2$ of Bn), 4.92-4.81 (m, 3H, $CH_2$ of Bn), 4.81-4.57 (m, 11H), 4.57-4.48 (m, 4H), 4.48-4.38 (m, 4H), 4.38-4.19 (m, 12H), 4.11-3.72 (m, 17H), 3.69 (dd, J=9.7, 7.0 Hz, 1H), 3.63-3.54 (m, 8H), 3.52 (t, J=6.4 Hz, 1H), 3.50-3.30 (m, 8H), 3.25 (dd, J=7.8, 3.9 Hz, 2H), 3.05 (dd, J=10.2, 3.7 Hz, 1H, $GlcNH_2$-2), 2.86 (q, J=7.3 Hz, 6H, $NCH_2CH_3$), 2.28 (t, 2H, —S—CH$_2$—CH$_2$—CH$_2$—CH$_2$—CH$_2$—CH$_2$—O), 2.23-2.08 (m, 4H, CH$_2$ of Lev), 1.83 (s, 3H, NHAc), 1.56-1.48 (m, 5H, CH$_3$ of Lev, —S—CH$_2$—CH$_2$—CH$_2$—CH$_2$—CH$_2$—CH$_2$—O), 1.42 (m$_{centered}$, 2H, —S—CH$_2$—CH$_2$—CH$_2$—CH$_2$—CH$_2$—CH$_2$—O), 1.26-1.14 (m, 13H, NCH$_2$CH$_3$, —S—CH$_2$—CH$_2$—CH$_2$—CH$_2$—CH$_2$—CH$_2$—O), 1.00-0.93 (m, 21H, TIPS); $^{13}$C NMR (151 MHz, CDCl$_3$) δ 205.92 (ketone of Lev), 171.77 (CO of Lev), 170.35 (CONN), 140.05, 139.05, 138.95, 138.88, 138.83, 138.75, 138.68, 138.58, 138.57, 138.40, 138.33, 138.24, 138.05, 137.99, 137.71, 128.92, 128.64, 128.62, 128.59, 128.57, 128.54, 128.46, 128.42, 128.40, 128.36, 128.32, 128.28, 128.26, 128.21, 128.14, 128.11, 128.09, 128.08, 128.00, 127.96, 127.84, 127.77, 127.72, 127.68, 127.67, 127.61, 127.56, 127.51, 127.49, 127.44, 127.28, 127.14, 126.97, 126.94, 100.58, 99.48, 98.79, 98.66, 96.51 (GlcNH$_2$-1), 81.99, 81.75, 81.23, 80.89, 80.52, 79.77, 79.24, 76.01, 75.76, 75.73, 75.57, 75.44, 75.34, 75.13, 74.76, 74.57, 74.40, 74.37, 74.26, 74.24, 74.20, 73.93, 73.85, 73.62, 73.27, 73.15, 72.96, 72.68, 72.40, 72.37, 72.32, 72.28, 72.09, 71.57, 71.49, 71.07, 70.77, 69.95 (ManI-2), 69.76, 68.98, 68.74, 66.74, 65.73, 65.69, 63.71 (GlcNH$_2$-2), 62.94, 53.25, 45.58, 37.90, 36.38, 31.46, 31.07, 31.02, 29.69, 29.30, 28.82, 28.06, 25.55, 23.22, 18.24, 18.18, 12.17, 8.74; $^{31}$P NMR (162 MHz, CDCl$_3$) δ −0.30; m/z (ESI) Found: [M+Na]$^+$, 3062.3573; C$_{177}$H$_{205}$N$_4$O$_{35}$PSSi requires [M+Na]$^+$, 3062.3577.

Example 2: Triethylammonium 2,3,4-Tri-O-benzyl-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-2-O-levulinyl-α-D-mannopyranosyl-(1→4)-2-azido-3,6-ucopyranosyl-O-benzyl-2-deoxy-α-D-glucopyranosyl-(1→6)-1-O-(6-(S-benzyl)thiohexyl phosphono)-2,3,4,5-tetra-O-benzyl-D-myo-inositol (compound 18)

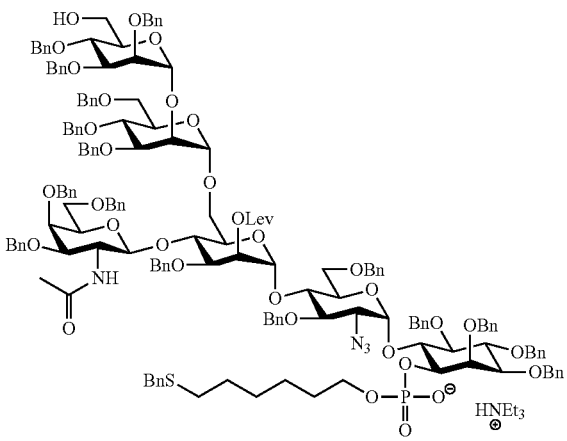

Triethylammonium 2,3,4-Tri-O-benzyl-6-O-triisopropylsilyl-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-2-O-levulinyl-α-D-mannopyranosyl-(1→4)-2-azido-3,6-di-O-benzyl-2-deoxy-α-D-glucopyranosyl-(1→6)-1-O-(6-(S-benzyl) thiohexyl phosphono)-2,3,4,5-tetra-O-benzyl-D-myo-inositol (compound 12) (59 mg, 19 μmol, 1 equiv) is dissolved in 2 mL MeCN. Water (13.5 μL, 0.75 mmol, 40 equiv) and Sc(TfO)$_3$ (18.5 mg, 38 μmol, 2 equ.) are added and the solution is heated up to 50° C. for 5 h. The reaction is quenched with pyridine (7.6 μL, 94 μmol, 5 equiv) and the solvents are removed in vacuo. The residue is purified through flash column chromatography (starting from CHCl3/MeOH 0%→5% MeOH) to yield colorless oil (52 mg, 18 μmol, 93%).

[α]$_D^{20}$=+31.3 (c=1.10 in CHCl$_3$); ν$_{max}$ (neat) 3346, 2925, 2107, 1742, 1719, 1669, 1497, 1454, 1362, 1048, 912 cm$^{-1}$; $^1$H NMR (600 MHz, CDCl$_3$) δ 7.43-6.88 (m, 85H), 6.01 (d, J=8.2 Hz, 1H, NH), 5.88 (d, J=3.7 Hz, 1H, GlcNH$_2$-1), 5.27-5.14 (m, 2H, ManI-2), 4.94 (m, 1H), 4.90-4.63 (m, 13H), 4.59 (d, J=10.7 Hz, 1H), 4.55-4.28 (m, 18H), 4.25-4.20 (m, 1H), 4.17 (dd, J=11.8, 5.3 Hz, 2H), 4.13-3.97 (m, 3H), 3.95 (t, J=2.2 Hz, 1H), 3.90 (t, J=9.6 Hz, 1H), 3.87-3.50 (m, 23H), 3.49-3.38 (m, 7H), 3.16 (dd, J=6.9, 3.1 Hz, 1H), 3.06 (dd, J=10.2, 3.7 Hz, 1H, GlcNH$_2$-2), 2.76 (q, J=7.2 Hz, 6H, NCH$_2$CH$_3$), 2.34-2.08 (m, 6H, CH$_2$ of Lev, —S—CH$_2$—CH$_2$—CH$_2$—CH$_2$—CH$_2$—CH$_2$—O), 1.85 (s, 3H, CH$_3$ of Lev), 1.64 (s, 3H, NHAc), 1.54-1.47 (m, 2H, —S—CH$_2$—CH$_2$—CH$_2$—CH$_2$—CH$_2$—CH$_2$—O), 1.45-1.37 (m, 2H, —S—CH$_2$—CH$_2$—CH$_2$—CH$_2$—CH$_2$—CH$_2$—O), 1.25-1.16 (m, 4H, —S—CH$_2$—CH$_2$—CH$_2$—CH$_2$—CH$_2$—CH$_2$—O), 1.13 (t, J=7.3 Hz, 9H, NCH$_2$CH$_3$); $^{13}$C NMR (151 MHz, CDCl$_3$) δ 206.17 (ketone of Lev), 171.72, 170.70, 140.03, 139.03, 138.87, 138.74, 138.69, 138.65, 138.62, 138.52, 138.48, 138.44, 138.41, 138.35, 138.19, 138.10, 138.00, 128.91, 128.63, 128.54, 128.53, 128.47, 128.45, 128.39, 128.36, 128.34, 128.33, 128.30, 128.28, 128.25, 128.11, 128.09, 128.08, 128.02, 128.00, 127.96, 127.81, 127.81, 127.77, 127.73, 127.67, 127.60, 127.56, 127.52, 127.47, 127.45, 127.43, 127.34, 127.24, 127.12, 126.93, 100.75, 99.86, 99.32, 98.90, 96.39 (GlcNH$_2$-1), 81.92, 81.79, 81.18, 80.09, 80.05, 79.55, 79.07, 76.08, 75.92, 75.72, 75.41, 75.26, 75.14, 75.10, 75.05, 74.94, 74.73, 74.55, 74.10, 73.95, 73.52, 73.48, 73.43, 73.09, 73.03, 72.42, 72.36, 72.29, 72.23, 72.18, 71.72, 71.28, 69.97, 69.67, 69.46 (ManI-2), 68.90, 68.67, 67.15, 65.71, 65.67, 63.39 (Glc-NH$_2$-2), 62.37, 54.27, 45.89 (NCH$_2$CH$_3$), 37.88, 36.36, 31.45 (—S—CH$_2$—CH$_2$—CH$_2$—CH$_2$—CH$_2$—CH$_2$—O), 31.06, 31.01, 29.70, 29.29, 28.81, 28.01, 25.54, 23.44, 9.62 (NCH$_2$CH$_3$); $^{31}$P NMR (243 MHz, CDCl$_3$) δ −1.08; m/z (ESI) Found: [M+Na]$^+$, 2922.2032; C$_{168}$H$_{185}$N$_4$O$_{35}$PSSi requires [M+Na]$^+$, 2922.1969.

Example 3: Bistriethylammonium 2,3,4-Tri-O-benzyl-6-O-(2-(N-benzyloxy carbonyl) aminoethyl phosphono)-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-α-D-mannopyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (compound 15)

stirred for 1 h and is quenched with hydrazine (1M in THF; 300 μL, 0.3 mmol, 17 equiv). The reaction mixture is stirred for 18 h. The solvents are removed in vacuo and the residue is purified through flash column chromatography (starting from CHCl3/MeOH: 97/3490/10) to yield yellow oil (49.5 mg, 15 μmol, 88%).

$[α]_D^{20}$=+32.5 (c=1.00 in CHCl$_3$); ν$_{max}$ (neat) 3387, 3063, 2929, 2108, 1672, 1497, 1057, 1029, 839 cm$^{-1}$; $^1$H NMR (400 MHz, CDCl$_3$) δ 7.37-6.90 (m, 90H), 6.28 (s, 1H, NHAc), 5.89 (d, J=3.5 Hz, 1H, GlcNH$_2$-1), 5.19 (d, J=1.6 Hz, 1H), 5.05-4.15 (m, 40H), 4.14-4.02 (m, 3H), 3.98-3.35

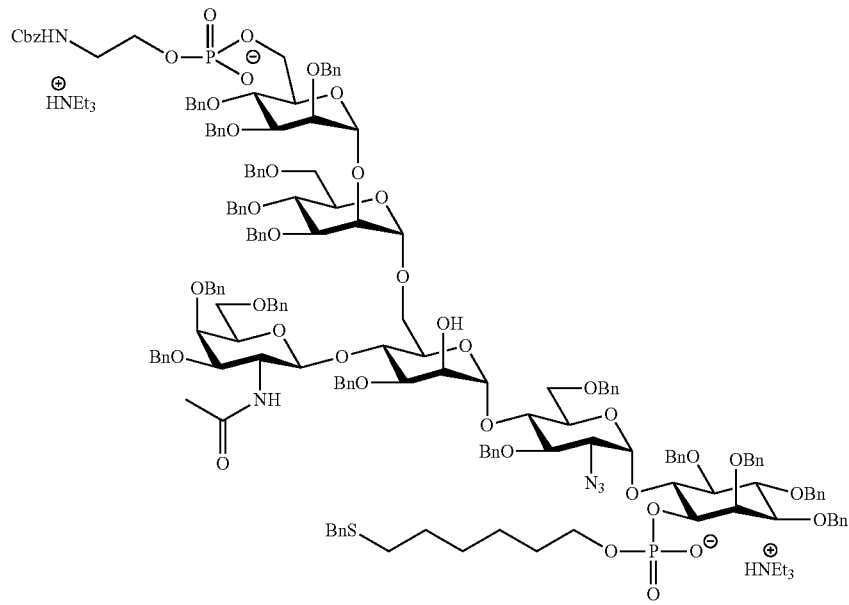

Triethylammonium 2,3,4-Tri-O-benzyl-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-2-O-levulinyl-α-D-mannopyranosyl-(1→4)-2-azido-3,6-di-O-benzyl-2-deoxy-α-D-glucopyranosyl-(1→6)-1-O-(6-(S-benzypthiohexyl phosphono)-2,3,4,5-tetra-O-benzyl-D-myo-inositol (compound 18) (28.3 mg, 78 μmol, 4.5 equiv) and triethylammonium 2-(((benzyloxy)carbonyl)amino)ethyl phosphonate (compound 13) (28.3 mg, 78 μmol, 4.5 equiv) are co evaporated 3 times with 2 mL dry pyridine. The residue is dissolved in 2 mL dry pyridine and PivCl (16.1 μL, 131 μmol, 7.5 equiv) is added. The solution is stirred for 2 h at r.t. before water (15.6 μL, 0.87 mmol, 50 equiv) and iodine (24.3 mg, 96 μmol, 5.5 equiv) are added. The red solution is (m, 36H), 3.28-3.20 (m, 1H), 3.14 (dd, J=9.2, 4.5 Hz, 1H), 3.05 (dd, J=10.2, 3.5 Hz, 1H, GlcNH$_2$-2), 2.61 (q, J=7.3 Hz, 12H, NCH$_2$CH$_3$), 2.28 (t, J=7.4 Hz, 2H, —S—CH$_2$—CH$_2$—CH$_2$—CH$_2$—CH$_2$—CH$_2$—O), 1.92-1.76 (m, 3H, COCH$_3$), 1.58-1.37 (m, 4H, —S—CH$_2$—CH$_2$—CH$_2$—CH$_2$—CH$_2$—CH$_2$—O), 1.26-1.13 (m, 4H, —S—CH$_2$—CH$_2$—CH$_2$—CH$_2$—CH$_2$—O), 0.97 (t, J=7.3 Hz, 18H, NCH$_2$CH$_3$); $^{13}$C NMR (151 MHz, CDCl$_3$) δ 170.84 (COCH$_3$), 156.58 (O(CO)NH), 138.71, 128.87, 128.50, 128.44, 128.36, 128.30, 128.21, 128.03, 127.94, 127.86, 127.76, 127.50, 126.91, 102.05, 101.15, 100.26, 98.71, 96.19, 82.02, 81.79, 81.06, 80.17, 80.03, 79.66, 77.37, 77.16, 76.95, 76.36, 75.93, 75.58, 75.19, 74.84, 74.80, 74.65, 74.03, 73.49, 72.79, 72.29, 71.62, 71.56, 71.49, 71.41, 70.08, 69.75, 69.64, 68.97, 66.34, 65.70, 65.04, 64.09, 63.49, 58.17, 45.70, 38.76, 36.34, 32.00, 31.44, 29.78, 29.59, 29.44, 29.27, 28.80, 27.54, 25.50, 22.77, 14.21, 8.71; $^{31}$P NMR (243 MHz, CDCl$_3$) δ −0.03, −1.67; m/z (ESI) Found: [M-H]$^-$, 3041.2393; C$_{173}$H$_{191}$N$_5$O$_{38}$P$_2$S requires [M-H]$^-$, 3041.2353.

Example 4: 6-O-(aminoethyl phosphono)-α-D-mannopyranosyl-(1→2)-α-D-mannopyranosyl-(1→6)-4-O-(2-deoxy-2-acetamido-β-D-galactopyranosyl)-α-D-mannopyranosyl-(1→4)-2-amino-2-deoxy-α-D-glucopyranosyl-(1→6)-1-O-(thiohexyl phosphono)-D-myo-inositol (Compound 3)

pound 15) (28 mg, 8.6 µmol) was dissolved in dry THF (1.5 mL) and added to the ammonium solution at −78° C. The reaction was stirred for 30 min at this temperature. The reaction was quenched with dry MeOH (2 mL) and the ammonia was blown off using a stream of nitrogen. The pH of the resulting solution was adjusted with concentrated acetic acid to 8-9. Solvents were removed in vacuo and the residue was purified using a small G10 column (GE Healthcare) to yield X as white solid (6.7 mg, 4.9 µmol, 58%): $^1$H NMR (600 MHz, D$_2$O) δ 5.54 (d, J=3.9 Hz, 1H, GlcNH$_2$), 5.23 (s, 1H), 5.19 (s, 1H), 5.03 (s, 1H), 4.51 (d, J=8.3 Hz, 1H, GalNAc-1), 4.29-3.66 (m, 36H), 3.63-3.53 (m, 2H), 3.45 (td, J=9.3, 4.3 Hz, 1H), 3.38 (dd, J=10.9, 4.3 Hz, 1H,

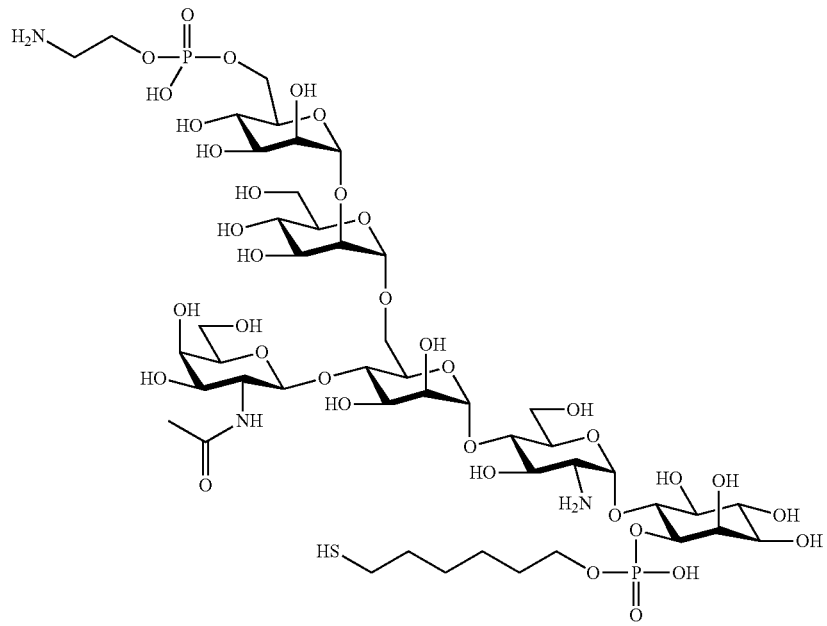

Approximately 10 mL ammonia were condensed in a flask and tert-BuOH (2 drops) was added. Afterwards small pieces of sodium were added till a dark blue colour was established. Bistriethylammonium 2,3,4-Tri-O-benzyl-6-O-(2-(N-benzyloxycarbonyl)aminoethyl phosphono)-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-α-D-mannopyranosyl-(1→4)-2-azido-3,6-di-O-benzyl-2-deoxy-α-D-glucopyranosyl-(1→6)-1-O-(6-(S-benzypthiohexyl phosphono)-2,3,4,5-tetra-O-benzyl-D-myo-inositol (com- GlcNH$_2$-2), 3.34-3.29 (m, 2H), 2.80 (t, J=7.1 Hz, 1H), 2.58 (t, J=7.1 Hz, 1H), 2.12 (s, 3H, Me of NHAc), 1.80-1.59 (m, 4H, linker), 1.51-1.36 (m, 4H, linker); $^{13}$C NMR (151 MHz, D$_2$O) δ 177.30 (amide), 105.02, 104.34 (GalNAc-1), 104.09, 101.16, 98.15 (Glc-NH$_2$-1), 81.69, 79.37, 78.78, 78.01, 75.69, 75.40, 74.84, 74.60, 74.05, 73.92, 73.62, 73.15, 73.08, 72.82, 72.64, 72.49, 72.03, 71.56, 70.32, 69.61, 69.21, 68.85, 67.28, 64.53, 64.50, 63.76, 63.70, 62.81, 56.64 (GlcNH$_2$-2), 55.19, 42.66, 40.73, 35.53, 32.31, 30.88, 29.67, 27.20, 27.00, 26.29, 24.96 (Me of NHAc); $^{31}$P NMR (243 MHz, D$_2$O) δ −2.62, −2.83; m/z (ESI) Found: [M−2H]$^{2-}$, 673.7104; C$_{46}$H$_{85}$N$_3$O$_{36}$P$_2$S requires [M−2H]$^{2-}$, 673.6981.

Example 5: Tristriethylammonium 2,3,4-Tri-O-benzyl-6-O-(2-(N-benzyloxycarbonyl)aminoethyl phosphono)-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-2-(2-(N-benzyloxycarbonyl)aminoethyl phosphono)-3-O-benzyl-α-D-mannopyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (Compound 16)

is added. The solution is stirred for 2 h at r.t. before water (10 μL, 0.56 mmol, 76 equiv) and iodine (6.8, 27 μmol, 5.5 equiv) are added. The red solution is stirred for 1 h and is quenched with sat. Na$_2$S$_3$O$_3$. The reaction mixture is diluted with 10 mL CHCl3 and dried over Na$_2$SO$_4$. The solvents are removed in vacuo and the residue is purified through flash column chromatography (CHCl3/MeOH 100/0480/20) to yield yellow oil (13.5 mg, 3.8 μmol, 76%).

$[\alpha]_D^{20}$=+22.0 (c=1.00 in CHCl$_3$); $\nu_{max}$ (neat) 3358, 2927, 2108, 1641, 1454, 1398, 1054, 7028, 838, 804 cm$^{-1}$; $^1$H NMR (600 MHz, CDCl$_3$) δ 7.56-6.77 (m, 90H), 6.44 (s, 2H, CbzNH), 6.22 (s, 1H, NHCOCH$_3$), 5.87 (s, 1H, GlcNH$_2$-1),

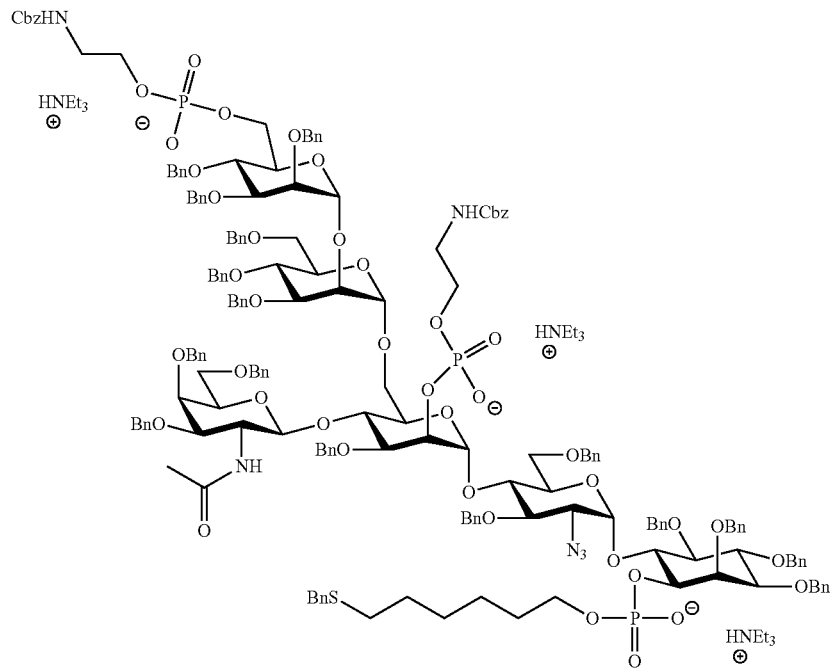

Bistriethylammonium 2,3,4-Tri-O-benzyl-6-O-(2-(N-benzyloxycarbonyl) aminoethyl phosphono)-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-3-O-benzyl-α-D-mannopyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (compound 15) (15 mg, 4.6 μmol, 1 equiv) and triethylammonium 2-(((benzyloxy)carbonyl)amino)ethyl phosphonate (compound 13) (8.1 mg, 22.5 μmol, 4.5 equiv) are co evaporated 3 times with 2 mL dry pyridine. The residue is dissolved in 2 mL dry pyridine and PivCl (4.6 μL, 36.8 μmol, 7.5 equiv)

5.49 (s, 1H), 5.09-3.35 (m, 83H), 3.30 (dd, J=14.2, 7.1 Hz, 1H), 3.26-3.17 (m, 2H), 3.17-3.08 (m, 2H), 3.07-2.79 (m, 1H), 2.58 (q, J=7.2 Hz, 18H, NCH$_2$CH$_3$), 2.27 (t, J=7.4 Hz, 2H, —S—CH$_2$—CH$_2$—CH$_2$—CH$_2$—CH$_2$—CH$_2$—O), 2.05-1.98 (m, 2H), 1.90-1.83 (m, 3H, NHCOCH$_3$), 1.59-1.36 (m, 4H, —S—CH$_2$—CH$_2$—CH$_2$—CH$_2$—CH$_2$—CH$_2$—O), 1.27-1.12 (m, 4H, —S—CH$_2$—CH$_2$—CH$_2$—CH$_2$—CH$_2$—O), 0.99 (t, J=7.2 Hz, 27H, NCH$_2$CH$_3$); $^{13}$C NMR (151 MHz, CDCl$_3$) δ 156.57 (OCONH), 140.07, 139.03, 138.78, 138.73, 138.67, 138.32, 137.23, 128.93, 128.54, 128.49, 128.44, 128.39, 128.36, 128.31, 128.28, 128.25, 128.23, 128.18, 128.03, 128.01, 127.97, 127.93, 127.82, 127.71, 127.60, 127.57, 127.54, 127.51, 127.41, 127.38, 127.30, 127.15, 127.06, 126.94, 126.84, 100.59, 98.53, 96.54 (GlcNH$_2$-1), 81.89, 81.20, 75.58, 75.04, 74.83, 74.67, 73.28, 72.84, 72.30, 66.39, 66.23, 65.70, 63.97, 45.85 (NCH$_2$CH$_3$), 42.97, 42.52, 40.10, 36.39, 34.58, 33.94, 32.05, 31.56, 31.50 (S—CH$_2$—CH$_2$—CH$_2$—CH$_2$—CH$_2$—CH$_2$—O), 31.08, 31.03, 30.33, 29.82, 29.79, 29.74, 29.63, 29.48, 29.32, 29.28, 29.08, 28.84, 25.55, 22.81, 21.56, 14.99, 14.30, 14.24, 13.23, 9.91 (NCH$_2$CH$_3$); $^{31}$P NMR (243 MHz, CDCl$_3$) δ 0.17, −0.02, −1.15; m/z (ESI) Found: [M+5Na−3H]$^{2+}$, 1705.6285; C$_{183}$H$_{203}$N$_6$O$_{43}$P$_3$S requires [M+5Na−3H]$^{2+}$, 1705.6062.

Example 6: 6-O-(aminoethyl phosphono)-α-D-mannopyranosyl-(1→2)-α-D-mannopyranosyl-(1→6)-2-O-(aminoethyl phosphono)-4-O-(2-deoxy-2-acetamido-β-D-galactopyranosyl)-α-D-mannopyranosyl-(1→4)-2-amino-2-deoxy-α-D-glucopyranosyl-(1→6)-1-O-(thiohexyl phosphono)-D-myo-inositol (Compound 5)

aminoethyl phosphono)-3-O-benzyl-α-D-mannopyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (compound 16) (22 mg, 6.1 μmol, 1 equiv) was dissolved in dry THF (15 mL) and dry tert-BuOH (0.1 mL). The solution is cooled down to −78° C. and approximately 20 mL ammonia is condensed in the flask. Afterwards small pieces of sodium are added. The solution is warmed to about −40° C. till a dark blue colour is established. Then the solution is cooled down to −78° C. and the reaction is stirred for 1 h at this temperature. The reaction is quenched with 2 mL dry MeOH and the ammonia is blown off of using a stream of nitrogen. Solvents are afterwards evaporated and the residue is dissolved in 5 mL water. The pH of the solution is adjusted with concentrated acetic acid to 4-7. Water is removed by freeze drying and the residue is purified using a small G25 column (1 cm×20 cm) to yield a white solid (2.6 mg, 1.8 μmol, 29%).

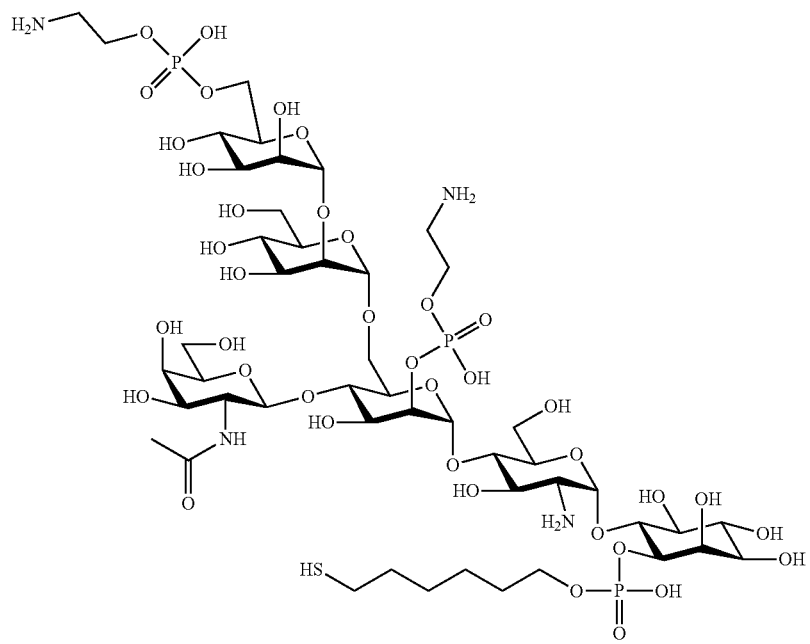

Tristriethylammonium 2,3,4-Tri-O-benzyl-6-O-(2-(N-benzyloxycarbonyl) aminoethyl phosphono)-α-D-mannopyranosyl-(1→2)-3,4,6-tri-O-benzyl-α-D-mannopyranosyl-(1→6)-4-O-(3,4,6-tri-O-benzyl-2-deoxy-2-acetamido-β-D-galactopyranosyl)-2-(2-(N-benzyloxycarbonyl)

$^1$H NMR (400 MHz, D$_2$O) δ 5.57-5.52 (m, 1H, GlcNH$_2$-1), 5.45 (s, 1H, ManI-1), 5.19 (s, 1H), 5.04 (s, 1H), 4.53 (d, J=8.4 Hz, 2H, GalNAc-1, ManI-2), 4.29-3.64 (m, 37H), 3.62-3.53 (m, 2H), 3.44 (t, J=9.3 Hz, 1H), 3.41-3.34 (m, 1H), 3.34-3.26 (m, 4H), 2.79 (t, J=7.3 Hz, 2H, HS—CH$_2$), 2.11 (s, 3H, Me of NHAc), 1.81-1.57 (m, 4H), 1.53-1.36 (m, 4H).; ³¹P NMR (162 MHz, D₂O) δ 0.36, 0.14, −0.81; m/z (ESI) Found: [M−3H]⁻³, 979.96; C₉₆H₁₈₀N₈O₇₈P₆S₂ requires [M−3H]⁻³, 979.93.

Example 7: Triethylammonium 2,3,4-Tri-O-benzyl-6-O-triisopropylsilyl-α-D-mannopyranosyl-(1→2)-3,4,6-tri-O-benzyl-α-D-mannopyranosyl-(1→6)-3-O-benzyl-4-O-(2,3,4,6-tetra-O-benzyl-α-D-glucopyranosyl-(1→4)-3,6-di-O-benzyl-2-deoxy-2-acetamido-β-D-galactopyranosyl)-2-O-levulinyl-α-D-manno-pyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (Compound 11)

times with 2 mL dry pyridine. The residue is dissolved in 2 mL dry pyridine and PivCl (14.5 μL, 118 μmol, 7.5 equiv) is added. The solution is stirred for 2 h at r.t. before water (14 μL, 0.79 mmol, 50 equiv) and iodine (29.9 mg, 118 μmol, 7.5 equiv) are added. The red solution is stirred for 1 h and is quenched with sat. Na₂S₂O₃. The reaction mixture is diluted with 10 mL CHCl3 and dried over Na₂SO₄. The solvents are removed in vacuo and the residue is purified through flash column chromatography (CHCl₃/MeOH 100/0495/5) to yield yellow oil (49 mg, 14 μmol, 87%).

[α]$_D^{20}$=+42.3 (c=1.00 in CHCl₃); ν$_{max}$ (neat) 3064, 3032, 2926, 2865, 2107, 1742, 1720, 1678, 1497, 1454, 1362, 1054, 1028, 913 cm⁻¹; ¹H NMR (600 MHz, CDCl₃) δ 7.49-6.87 (m, 100H), 6.07 (d, J=9.0 Hz, 1H, NH), 5.78 (s, 1H), 5.25 (s, 2H, ManI-2), 5.07 (s, 1H), 4.94 (d, J=11.9 Hz, 1H, CH₂ of Bn), 4.89-3.89 (m, 49H), 3.86-3.74 (m, 11H),

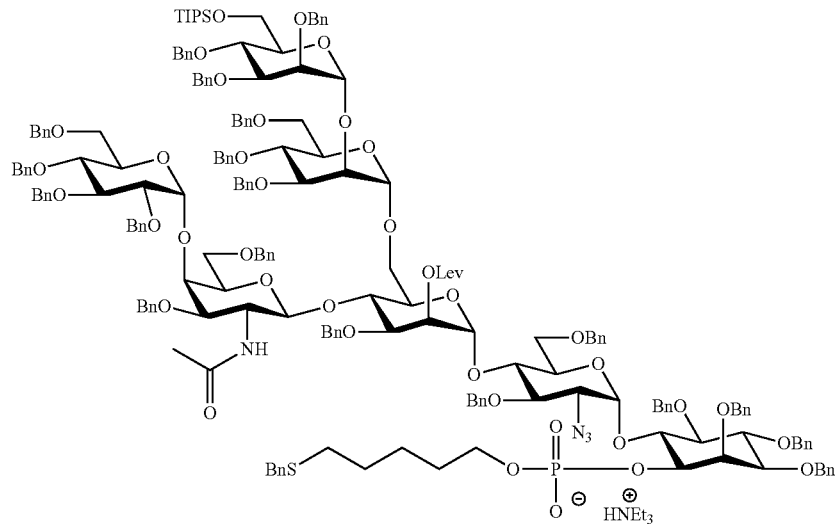

2,3,4-Tri-O-benzyl-6-O-triisopropylsilyl-α-D-mannopyranosyl-(1→2)-3,4,6-tri-O-benzyl-α-D-mannopyranosyl-(1→6)-3-O-benzyl-4-O-(2,3,4,6-tetra-O-benzyl-α-D-glucopyranosyl-(1→4)-3,6-di-O-benzyl-2-deoxy-2-acetamido-β-D-galactopyranosyl)-2-O-levulinyl-α-D-manno-pyranosyl-(1→4)-2-azido-3,6-di-O-benzyl-2-deoxy-α-D-glucopyranosyl-(1→6)-2,3,4,5-tetra-O-benzyl-D-myo-inositol (compound 8) (50 mg, 16 μmol, 1 equiv) and triethylammonium 6-(benzylthio)hexyl phosphonate (compound 10) (39 mg, 100 μmol, 6.4 equ.) are co evaporated 3

3.73-3.66 (m, 2H), 3.63 (dd, J=8.9, 2.9 Hz, 1H), 3.60-3.45 (m, 11H), 3.44-3.36 (m, 4H), 3.34-3.22 (m, 5H), 3.03 (dd, J=10.1, 3.6 Hz, 1H), 2.85 (q, J=7.3 Hz, 6H, NCH₂CH₃), 2.78 (d, J=9.4 Hz, 1H), 2.27 (t, J=7.4 Hz, 2H, BnS—CH₂), 2.24-2.04 (m, 4H, CH₂ of Lev), 1.80 (s, 3H, CH₃ of Lev), 1.70 (s, 3H, NHCOCH₃), 1.55-1.34 (m, 4H, —S—CH₂—CH₂—CH₂—CH₂—CH₂—CH₂—O), 1.23-1.16 (m, 4H, —S—CH₂—CH₂—CH₂—CH₂—CH₂—CH₂—O), 1.12 (t, J=7.6 Hz, 9H, NCH₂CH₃), 1.00-0.94 (m, 21H, TIPS); ¹³C NMR (151 MHz, CDCl₃) δ 205.92 (ketone of Lev), 171.76

(CO of Lev), 170.21 (NHCOCH₃), 140.02, 139.09, 139.03, 138.94, 138.91, 138.84, 138.76, 138.74, 138.69, 138.60, 138.57, 138.30, 138.15, 138.10, 138.01, 137.54, 128.92, 128.77, 128.72, 128.65, 128.62, 128.57, 128.54, 128.46, 128.44, 128.39, 128.36, 128.33, 128.31, 128.28, 128.27, 128.25, 128.24, 128.22, 128.16, 128.12, 128.10, 128.07, 127.98, 127.87, 127.84, 127.82, 127.77, 127.71, 127.67, 127.65, 127.63, 127.57, 127.55, 127.52, 127.48, 127.44, 127.29, 127.27, 127.18, 127.14, 126.94, 126.45, 101.71, 100.84, 99.65, 98.84, 98.65, 96.71, 82.20, 81.99, 81.51, 81.19, 81.03, 80.51, 80.12, 79.80, 79.13, 77.95, 77.53, 76.81, 75.93, 75.74, 75.43, 75.35, 75.26, 75.15, 74.75, 74.69, 74.54, 74.43, 74.03, 73.86, 73.63, 73.48, 73.23, 73.20, 73.00, 72.85, 72.39, 72.36, 72.07, 71.53, 71.37, 70.88, 70.79, 70.06 (ManI-2), 69.67, 68.77, 68.59, 67.74, 66.87, 65.80, 63.72, 62.90, 52.87, 45.42 (NCH₂CH₃), 38.57, 37.83, 36.38, 31.46, 31.00, 30.95, 29.82, 29.66, 29.30 (CH₃ of Lev), 28.81, 28.04, 27.69, 27.41, 25.52, 23.31 (NHCOCH₃), 18.24, 18.18, 14.25, 12.18, 8.55 (NCH₂CH₃); $^{31}$P NMR (243 MHz, CDCl₃) δ −1.45; m/z (ESI) Found: [M−2H]$^{2−}$, 1734.7564; C₂₀₄H₂₃₃N₄O₄₀PSSi requires [M−2H]$^{2−}$, 1734.7730.

Example 8: Triethylammonium 2,3,4-Tri-O-benzyl-α-D-mannopyranosyl-(1→2)-3,4,6-tri-O-benzyl-α-D-mannopyranosyl-(1→6)-3-O-benzyl-4-O-(2,3,4,6-tetra-O-benzyl-α-D-glucopyranosyl-(1→4)-3,6-di-O-benzyl-2-deoxy-2-acetamido-β-D-galactopyranosyl)-2-O-levulinyl-α-D-manno-pyranosyl-(1→4)-2-azido-3,6-di-O-benzyl-2-deoxy-α-D-glucopyranosyl-(1→6)-1-O-(6-(S-benzyl) thiohexyl phosphono)-2,3,4,5-tetra-O-benzyl-D-myo-inositol (Compound 17)

mannopyranosyl-(1→6)-3-O-benzyl-4-O-(2,3,4,6-tetra-O-benzyl-α-D-glucopyranosyl-(1→4)-3,6-di-O-benzyl-2-deoxy-2-acetamido-β-D-galactopyranosyl)-2-O-levulinyl-α-D-manno-pyranosyl-(1→4)-2-azido-3,6-di-O-benzyl-2-deoxy-α-D-glucopyranosyl-(1→6)-1-O-(6-(S-benzyl) thiohexyl phosphono)-2,3,4,5-tetra-O-benzyl-D-myo-inositol (compound 11) (43 mg, 12 μmol, 1 equiv) is dissolved in 2 mL MeCN. Water (8.7 μL, 0.48 mmol, 40 equiv) and Sc(TfO)₃ (11.8 mg, 24 μmol, 2 equiv) are added and the solution is heated up to 50° C. for 5 h. The reaction is quenched with pyridine (4.8 μL, 60 μmol, 5 equiv) and the solvents are removed in vacuo. The residue is purified through flash column chromatography (CHCl₃/MeOH 100/0→95/5) to yield colorless oil (32 mg, 9.4 μmol, 78%).

[α]$_D^{20}$=+47.4 (c=1.00 in CHCl₃); ν$_{max}$ (neat) 3363, 3031, 2926, 2862, 2107, 1742, 1719, 1671, 1497, 1454, 1362, 1068, 1049, 1028, 697 cm$^{-1}$; $^1$H NMR (600 MHz, CDCl₃) δ 7.55-6.71 (m, 100H), 6.19 (s, 1H, NH), 5.87 (s, 1H), 5.20 (s, 1H), 5.17 (s, 1H), 5.03-4.16 (m, 40H), 4.15-3.33 (m, 43H), 3.28 (d, J=10.6 Hz, 1H), 3.21-3.11 (m, 1H), 3.02 (d, J=7.7 Hz, 1H), 2.87 (d, J=10.1 Hz, 1H), 2.80 (q, J=7.0 Hz, 6H, NCH₂CH₃), 2.35-2.13 (m, 6H, BnS—CH₂, CH₂ of Lev), 1.85 (s, 3H, CH₃ of Lev), 1.75 (s, 3H, NHCOCH₃), 1.59-1.35 (m, 4H, —S—CH₂—CH₂—CH₂—CH₂—CH₂—CH₂—O), 1.28-1.13 (m, 4H, —S—CH₂—CH₂—CH₂—CH₂—CH₂—CH₂—O), 1.10 (t, J=7.3 Hz, 1H, NCH₂CH₃);
$^{13}$C NMR (151 MHz, CDCl₃) δ 206.20 (ketone of Lev), 171.68 (CO of Lev), 170.78 (NHCO), 149.97, 140.04, 139.04, 138.99, 138.87, 138.78, 138.68, 138.64, 138.54, 138.49, 138.30, 138.20, 138.10, 128.93, 128.82, 128.55, 128.49, 128.48, 128.43, 128.39, 128.37, 128.33, 128.30, 128.17, 128.08, 128.03, 127.96, 127.90, 127.80, 127.75, 127.66, 127.62, 127.59, 127.55, 127.53, 127.45, 127.35, 127.12, 126.95, 126.82, 101.45, 100.42, 100.04, 99.52, 99.19, 96.41, 82.15, 81.91, 81.21, 80.37, 79.99, 79.65,

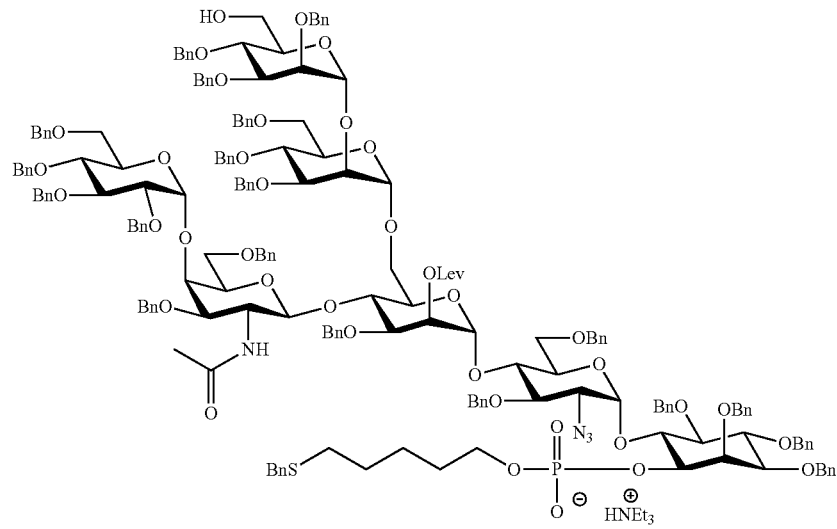

Triethylammonium 2,3,4-Tri-O-benzyl-6-O-triisopropyl-silyl-α-D-mannopyranosyl-(1→2)-3,4,6-tri-O-benzyl-α-D-

77.96, 76.20, 75.86, 75.70, 75.36, 75.29, 75.13, 75.04, 74.93, 74.74, 74.10, 73.60, 73.53, 73.36, 73.29, 73.00, 72.56, 72.37, 72.31, 72.26, 72.17, 71.69, 71.20, 70.79, 69.84, 69.48, 69.26 (ManI-2), 69.00 67.98, 67.79, 65.75, 65.71, 63.32, 62.50, 54.82, 45.44 ($NCH_2CH_3$), 37.88, 36.39, 32.06, 31.47, 31.06, 29.91, 29.83, 29.72, 29.45, 29.39, 29.31, 28.84, 28.03, 27.71, 27.36, 25.55, 23.59, 22.83, 17.85, 14.26, 12.43, 8.60 ($NCH_2CH_3$); $^{31}$P NMR (243 MHz, $CDCl_3$) δ −1.12; m/z (ESI) Found: $[M+Cl-H]^{2-}$, 1673.6842; $C_{195}H_{213}N_4O_{40}PS$ requires $[M+Cl-H]^{2-}$, 1673.6918.

Example 9: Bistriethylammonium 2,3,4-Tri-O-benzyl-6-O-(2-(N-benzyloxycarbonyl)aminoethyl phosphono)-α-D-mannopyranosyl-(1→2)-3,4,6-tri-O-benzyl-α-D-mannopyranosyl-(1→6)-3-O-benzyl-4-O-(2,3,4,6-tetra-O-benzyl-α-D-glucopyranosyl-(1→4)-3,6-di-O-benzyl-2-deoxy-2-acetamido-β-D-galactopyranosyl)-α-D-manno-pyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (Compound 14)

pound 17) (31 mg, 9.1 µmol, 1 equiv) and triethylammonium 2-(((benzyloxy)carbonyl)amino)ethyl phosphonate (compound 13) (14.7 mg, 41 µmol, 4.5 equiv) are co evaporated 3 times with 2 mL dry pyridine. The residue is dissolved in 2 mL dry pyridine and PivCl (8.4 µL, 68 µmol, 7.5 equiv) is added. The solution is stirred for 2 h at r.t. before water (8.2 µL, 0.45 mmol, 50 equiv) and iodine (12.7 mg, 50 µmol, 5.5 equiv) are added. The red solution is stirred for 1 h and is quenched with hydrazine (1M in THF, 227 µL, 0.28 mmol, 25 equiv). The reaction mixture is stirred for 18 h. The solvents are removed in vacuo and the residue is purified through flash column chromatography ($CHCl_3$/MeOH 100/0→90/10) to yield yellow oil (25.3 mg, 6.9 µmol, 76%).

$[a]_D^{20}$=+46.0 (c=1.00 in $CHCl_3$); $v_{max}$ (neat) 3344, 2926, 2864, 2108, 1683, 1497, 1454, 1363, 1093, 1071, 1028, 863 $cm^{-1}$; $^1$H NMR (600 MHz, $CDCl_3$) δ 7.38-6.79 (m, 105H), 6.23 (s, 1H, $NHCOCH_3$), 5.87 (d, J=3.4 Hz, 1H), 5.15 (s, 1H), 5.00-3.30 (m, 90H), 3.24 (d, J=10.3 Hz, 1H), 3.11 (d, J=4.6 Hz, 1H), 3.03 (d, J=8.0 Hz, 1H), 2.80 (d, J=10.2 Hz, 1H), 2.69 (q, J=7.2 Hz, 12H, $NCH_2CH_3$), 2.28 (t, J=7.4 Hz, 2H, BnS—$CH_2$), 1.86 (s, 1H, $NHCOCH_3$), 1.59-1.36 (m, 4H, —S—$CH_2$—$CH_2$—$CH_2$—$CH_2$—$CH_2$—$CH_2$—O),

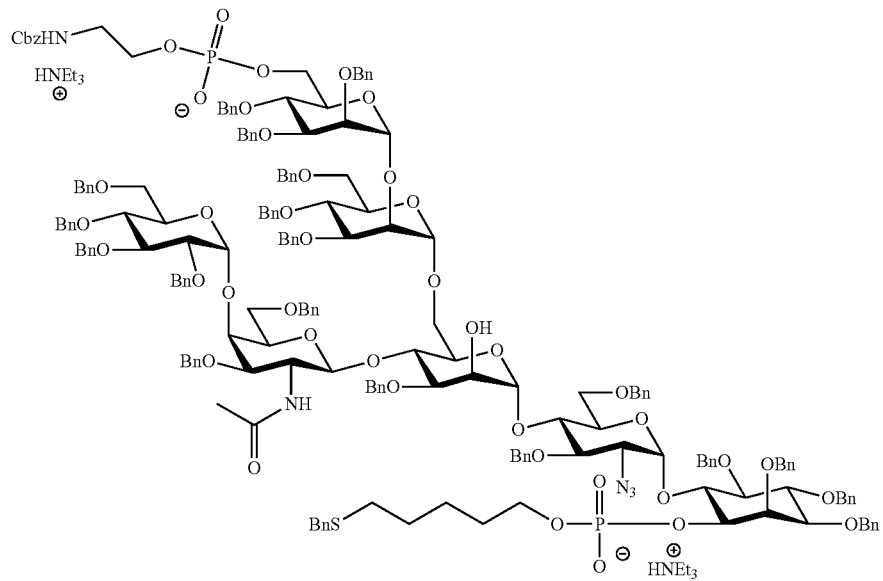

Triethylammonium 2,3,4-Tri-O-benzyl-α-D-mannopyranosyl-(1→2)-3,4,6-tri-O-benzyl-α-D-mannopyranosyl-(1→6)-3-O-benzyl-4-O-(2,3,4,6-tetra-O-benzyl-α-D-glucopyranosyl-(1→4)-3,6-di-O-benzyl-2-deoxy-2-acetamido-β-D-galactopyranosyl)-2-O-levulinyl-α-D-mannopyranosyl-(1→4)-2-azido-3,6-di-O-benzyl-2-deoxy-α-D-glucopyranosyl-(1→6)-1-O-(6-(S-benzyl)thiohexyl phosphono)-2,3,4,5-tetra-O-benzyl-D-myo-inositol (com- 1.26-1.11 (m, 4H, —S—$CH_2$—$CH_2$—$CH_2$—$CH_2$—$CH_2$—$CH_2$—O), 1.02 (t, J=7.3 Hz, 18H, $NCH_2CH_3$); $^{13}$C NMR (151 MHz, $CDCl_3$) δ 169.72 ($NHCOCH_3$), 155.80 (O—CO—NH), 139.25, 138.46, 138.30, 138.23, 137.98, 137.70, 137.48, 137.27, 137.00, 136.33, 128.69, 128.25, 128.19, 128.13, 127.85, 127.79, 127.62, 127.27, 127.13, 127.07, 126.80, 126.74, 126.54, 126.26, 125.68, 101.37, 100.31, 99.20, 98.96, 98.52, 94.76, 81.97, 81.82, 81.78, 81.51, 80.99, 80.93, 80.86, 80.84, 80.52, 80.17, 79.87, 79.48, 79.22, 78.90, 78.51, 77.79, 77.30, 75.92, 75.62, 74.89, 74.68, 74.57, 74.19, 73.94, 73.35, 72.99, 72.41, 72.11, 71.48, 71.20, 71.01, 70.46, 69.50, 69.23, 68.93, 67.83, 67.04, 66.60, 66.06, 65.93, 65.65, 64.95, 64.68, 64.19, 64.01, 63.31, 63.23, 62.40, 62.26, 52.47, 51.52, 45.62, 44.66, 43.74, 36.52, 35.62, 34.73, 31.66, 31.10, 30.71, 30.29 (BnS—CH$_2$), 29.89, 29.82, 29.40, 29.06, 28.55, 28.23, 28.08, 27.72, 27.25, 26.36, 25.59, 24.80, 23.96, 23.12, 22.28 (NHCOCH$_3$), 9.11, 8.26, 7.41, 6.56; $^{31}$P NMR (243 MHz, CDCl$_3$) δ 0.00, −1.32; m/z (ESI) Found: [M−2H]$^{2-}$, 1735.2054; C$_{200}$H$_{219}$N$_5$O$_{43}$P$_2$S requires [M−2H]$^{2-}$, 1735.2077.

Example 10: 6-O-(aminoethyl phosphono)-α-D-mannopyranosyl-(1→2)-α-D-mannopyranosyl-(1→6)-4-O-(α-D-glucopyranosyl-(1→4)-2-deoxy-2-acetamido-β-D-galactopyranosyl)-α-D-mannopyranosyl-(1→4)-2-amino-2-deoxy-α-D-glucopyranosyl-(1→6)-1-O-(thiohexyl phosphono)-D-myo-inositol (Compound 4)

are added till a dark blue colour is established. Then the solution is stirred for 35 min at this temperature. The reaction is quenched with 2 mL dry MeOH and the ammonia is blown off of using a stream of nitrogen. Solvents are afterwards evaporated and the residue is dissolved in 5 mL water. The pH of the solution is adjusted with concentrated acetic acid to 7. Water is removed by freeze drying and the residue is purified using a small G25 column (1 cm×20 cm) to yield a white solid (4.5 mg, 3.0 µmol, 55%).

ν$_{max}$ (neat) 3350, 2918, 1646, 1025 cm$^{-1}$; $^1$H NMR (400 MHz, D$_2$O) δ 5.59 (d, J=3.6 Hz, 1H, GlcNH$_2$-1), 5.27 (s, 1H), 5.23 (s, 1H), 5.07 (s, 1H), 4.99 (d, J=3.8 Hz, 1H, Glc-1), 4.60 (d, J=8.2 Hz, 1H, GalNAc-1), 4.31-3.67 (m, 39H), 3.60 (dd, J=10.1, 3.6 Hz, 2H), 3.55-3.39 (m, 3H), 3.35 (t, 2H), 2.83 (t, J=7.2 Hz, 1H), 2.61 (t, J=7.1 Hz, 1H), 2.14 (s, 3H), 1.82-1.58 (m, 4H), 1.54-1.38 (m, 4H); $^{13}$C NMR (151 MHz, D$_2$O) δ 177.28 (amide), 105.01, 104.76 (GalNAc-1), 103.91, 102.82 (Glc-1), 101.11, 99.97 (GlcNH$_2$-1), 81.64, 79.91, 79.30, 79.25, 79.15, 78.84, 78.04, 75.70, 75.69, 75.39, 75.36, 75.29, 74.84, 74.61, 74.55, 74.40, 74.32, 74.08, 73.94, 73.62, 73.16, 72.86, 72.83, 72.66,

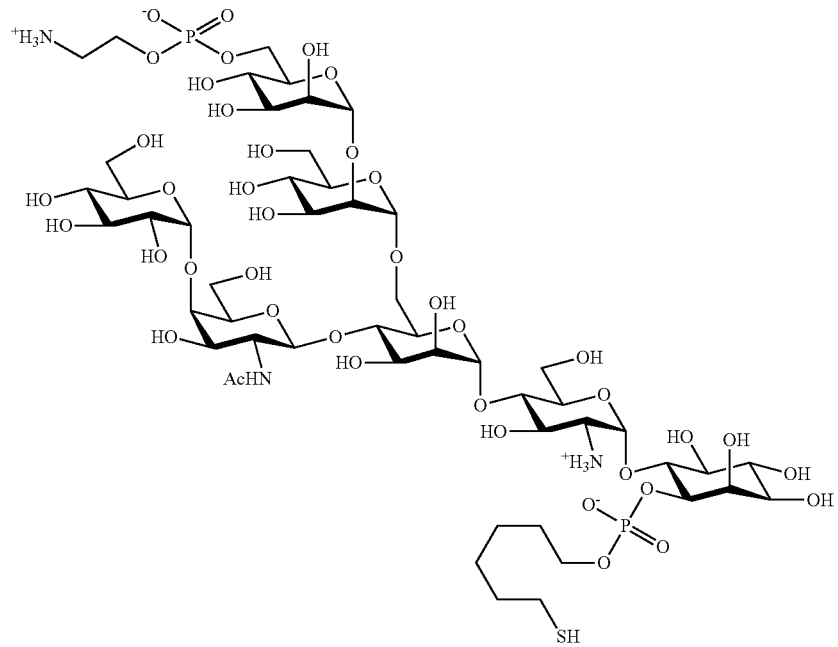

Bistriethylammonium 2,3,4-Tri-O-benzyl-6-O-(2-(N-benzyloxycarbonyl)aminoethyl phosphono)-α-D-mannopyranosyl-(1→2)-3,4,6-tri-O-benzyl-α-D-mannopyranosyl-(1→6)-3-O-benzyl-4-O-(2,3,4,6-tetra-O-benzyl-α-D-glucopyranosyl-(1→4)-3,6-di-O-benzyl-2-deoxy-2-acetamido-β-D-galactopyranosyl)-α-D-manno-pyranosyl-(1→4)-2-azido-3,6-di-O-benzyl-2-deoxy-α-D-glucopyranosyl-(1→6)-1-O-(6-(S-benzypthiohexyl phosphono)-2,3,4,5-tetra-O-benzyl-D-myo-inositol (compound 14) (20 mg, 5.4 µmol, 1 equiv) was dissolved in dry THF (3 mL) and dry tert-BuOH (2 drops). The solution is cooled down to −78° C. and approximately 10 mL ammonia is condensed in the flask. Afterwards small pieces of sodium 72.58, 72.55, 72.50, 72.27, 72.18, 72.12, 72.06, 71.82, 71.62, 69.60, 69.22, 68.87, 67.29, 64.51, 64.48, 63.77, 62.98, 62.82, 62.52, 56.58, 55.08, 42.72, 42.67, 40.75, 35.52, 32.28, 30.88, 29.80, 29.67, 27.30, 27.18, 26.99, 26.52, 26.29, 25.84, 24.96; $^{31}$P NMR (162 MHz, D$_2$O) δ 0.40, 0.22; m/z (ESI) Found: [M−H]$^-$, 1510.4612; C$_{52}$H$_{93}$N$_3$O$_{41}$P$_2$S requires [M−H]$^-$, 1510.4564.

Part A2: Preparation of Sulfone Linked Thiol Functionalized GPI

Figure 2:
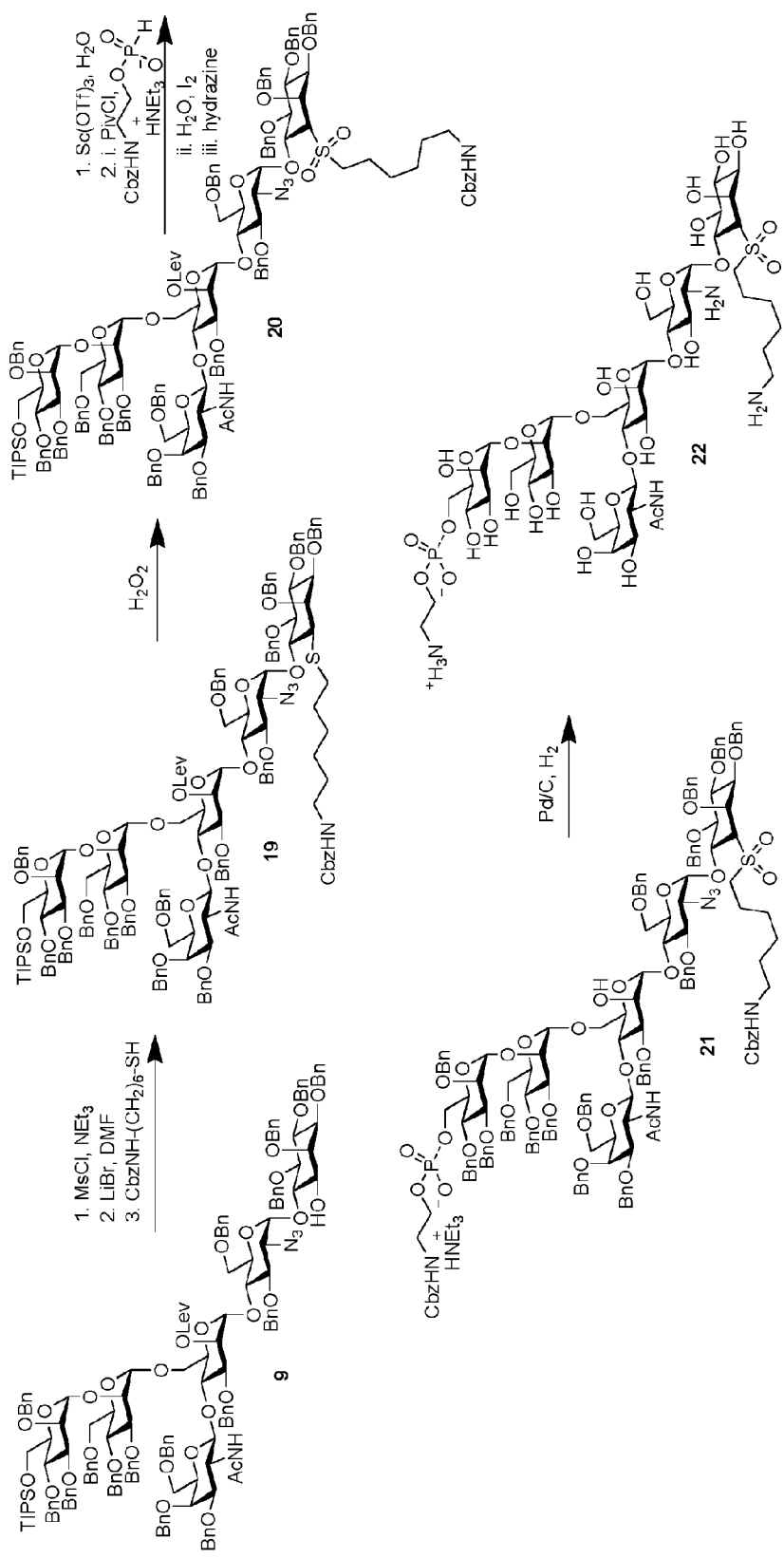
FIG. 2: Reaction scheme for the preparation of glycan 22 as example for a sulfone linked GPI.

Formation of the mesilate ester with mesityl chloride and triethylamine followed by a S$_{N2}$ reaction leads to bromide 19a that is substituted by the thiol linker under inversion of stereochemistry to generate 19. Oxidation with hydrogen peroxide yields the sulfone 20, which is deprotected under acidic conditions. Introduction of a protected phosphoethanolamine and cleavage of the levulinic ester using hydrazine produces oligosaccharide 21. Final hydrogenolysis yields glycan 22 ready for conjugation. The reaction scheme is shown under FIG. 2.

B Experimental Data for Vaccination

Example 11: Conjugation to a Carrier

Vaccines based on polysaccharides are characterized by a T-cell independent immune response without inducing an immunological memory. Immunogenicity of polysaccharide vaccines in infants, elderly and immunocompromised patients are weak. Conjugation of carbohydrates to a carrier, such as a carrier protein or a glycosphingolipid with immnunomodulatory properties, creates a T-cell dependent immune response against the carbohydrate. As carrier protein, the nontoxic diphtheria toxoid variant $CRM_{197}$ was used, since it has been approved as a constituent of licensed vaccines.

Figure 6:
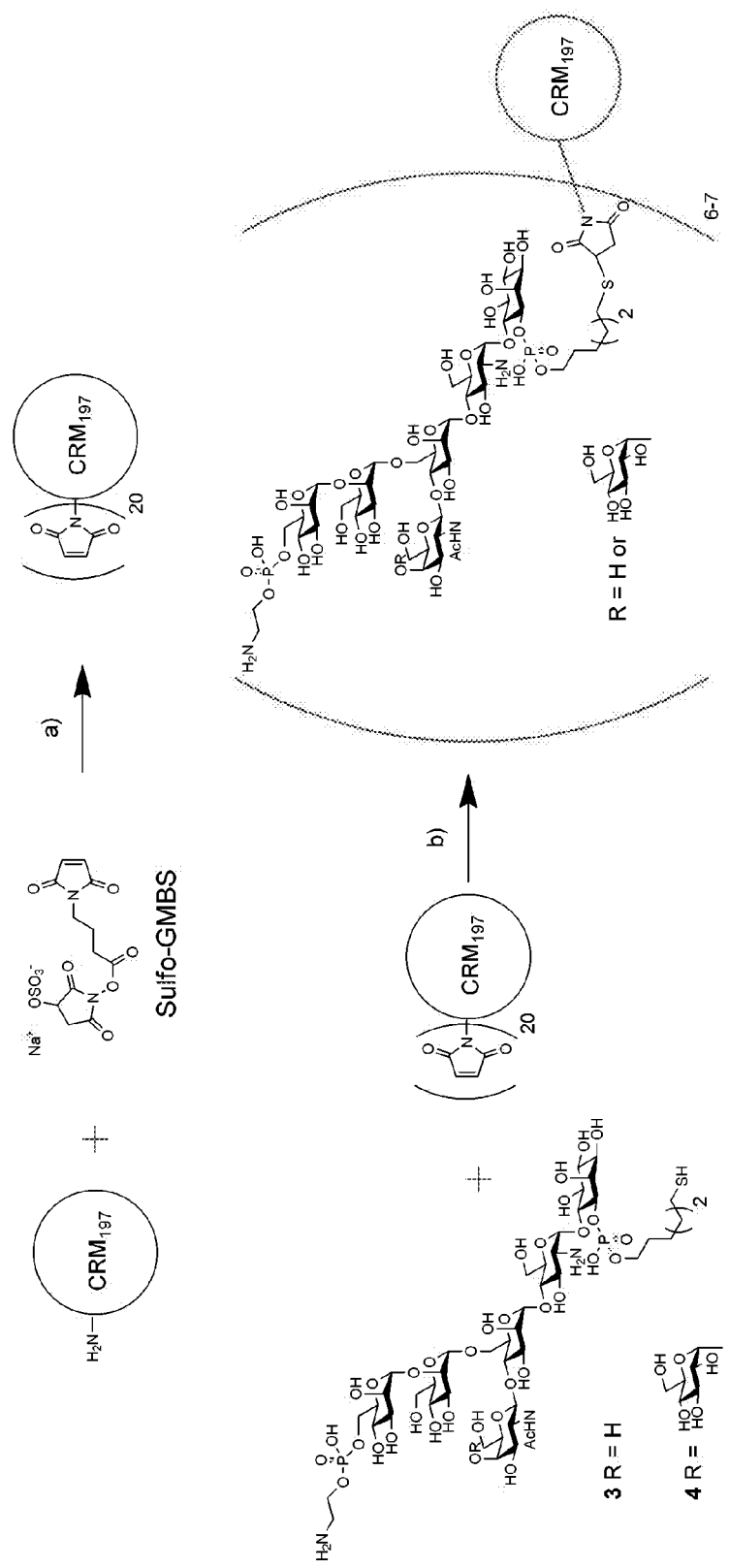
FIG. 6: Preparation of conjugates of compounds 3 and 4 with $CRM_{197}$ for immunization: a) maleimide-modification of $CRM_{197}$ PBS, pH=7.4, room temperature, 2 h b) coupling of compounds 3 and 4: PBS, pH=7.4, room temperature, 3 h.
Figure 7:
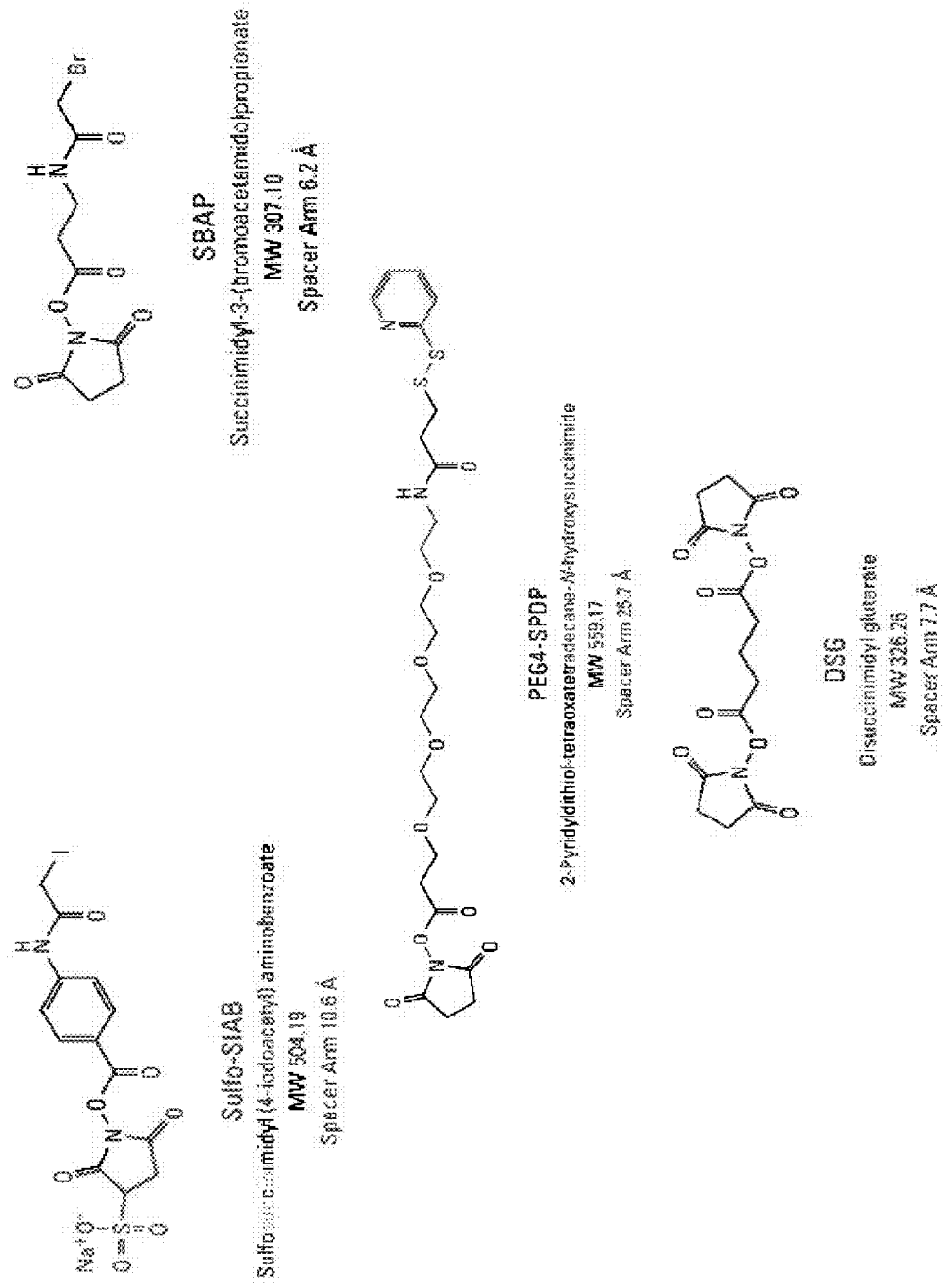
FIG. 7: Selection of reactive bifunctional molecules A suitable for modifying a carrier material for subsequent introduction of a compound of the formula (I) on the carrier material by direct bonding.

Example 11a: Conjugation to a Maleimide-Modified Protein (FIG. 6)

1 mg (17 nmol) $CRM_{197}$ was dissolved in 500 µL PBS to yield a 40 µM $CRM_{197}$ solution. 3 mg Sulfo-GMBS (Pierce) was dissolved in 500 µL PBS (1.6 mM, 40 equiv.) and added to the protein solution. The solution was incubated for 2 h at room temperature, before it was concentrated and washed with water (4×500 µL) in an Amicon Ultra-0.5 mL centrifugal filter (Millipore™). Afterwards 250 µg (170 nmol) of GPI 3 was incubated with an equimolar amount of TCEP for 1 h in 500 µL PBS. The GPI solution was added to the concentrated maleimide-modified $CRM_{197}$ and the solution was incubated for 3 h at room temperature. The conjugate was purified using a G25 column (10 mm×140 mm, eluent 5% EtOH in water) and the fractions containing the protein were identified using Bradford solution. The fractions containing the conjugate were pooled and the protein concentration was determined by BCA Protein Assay (Pierce). Finally the solution was lyophilized to yield the conjugate as a white solid. Purity and loading were determined via MALDI mass analysis.

Example 11b: In Batch Conjugation to an Olefin-Modified Protein at 254 nm

Compound of general formula (I) (10 equiv.) and olefin-modified $CRM_{197}$ (1 equiv., p. Angew. Chem. 2007, 119, 5319) were dissolved in a quartz glass reaction vessel under argon atmosphere in degassed PBS at pH=7.4. The solution was stirred for 6 h under irradiation with light emitted by a low pressure mercury lamp (λ=254, 77 W). Afterwards the solution was frozen dried and the crude material was purified using size exclusion chromatography (Sephadex-G25, 5% EtOH in water, 10 mm×150 mm) to yield the conjugates of the compound of general formula (I) covalently linked to the olefin modified $CRM_{197}$, as white solids.

Example 11c: In Flow Conjugation to an Olefin-Modified Protein at 254 nm

By using a photochemical flow reactor (Chem. Eur. J. 2013, 19, 3090) that was fitted with a loop of Teflon AF2400 tubing (566 µL), a solution of compound of general formula (I) (10 equiv.) in water (300 µL) was reacted with olefin-modified $CRM_{197}$ (1 equiv., Angew. Chem. 2007, 119, 5319) in water (300 µL) and AcOH (8 µL; residence time: 10 min, flow rate: 28.3 µL/min$^{-1}$ per syringe). The reactor output was lyophilized and the crude material was purified using size exclusion chromatography (Sephadex-G25, 5% EtOH in water, 10 mm×150 mm) to yield the conjugates of the compounds of general formula (I) covalently linked to the olefin modified $CRM_{197}$ as white solid.

Example 11d: In Flow Conjugation to an Olefin-Modified Protein at 366 nm

By using a photochemical flow reactor (Chem. Eur. J. 2013, 19, 3090) that was fitted with a loop of Teflon AF2400 tubing (566 µL), a solution of compound of general formula (I) (10 equiv.) in water (300 µL) was reacted with olefin modified $CRM_{197}$ (1 equiv., Angew. Chem. 2007, 119, 5319) in water (300 µL) and AcOH (8 µL; residence time: 30 min, flow rate: 9.4 µL/min$^{-1}$ per syringe). The reactor output was lyophilized and the crude material was purified using size exclusion chromatography (Sephadex-G25, 5% EtOH in water, 10 mm×150 mm) to yield the conjugate of the compound of general formula (I) covalently linked to the olefin modified $CRM_{197}$ as white solid.

Example 11e: Conjugation to a α-Iodoacetamide-Modified Protein

Figure 8:
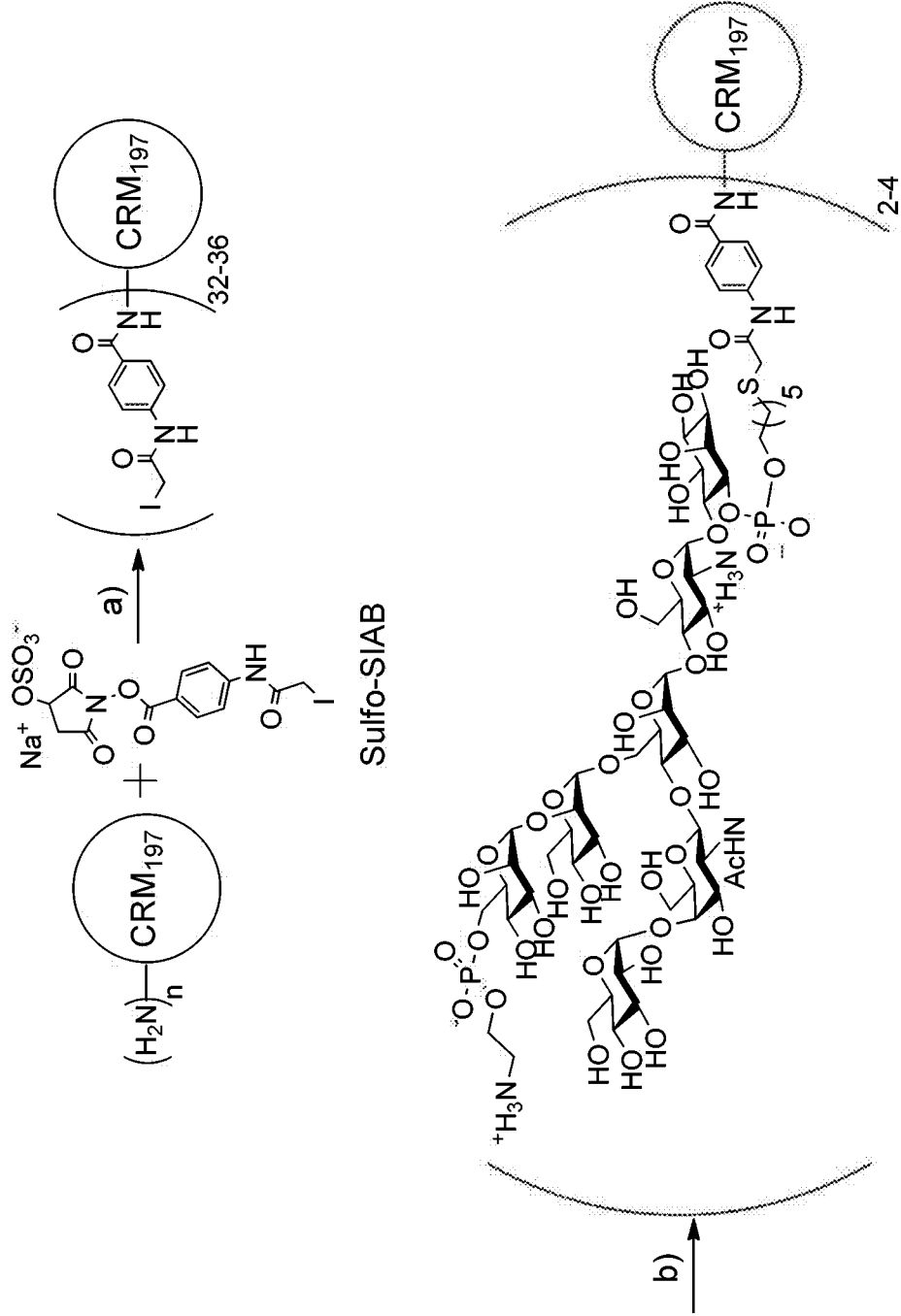
FIG. 8: Preparation of the conjugate of compound 4 with $CRM_{197}$ for immunization: a) α-iodoacetamide modification of $CRM_{197}$: PBS, pH=7.4, 1 h, room temperature; b) coupling of compound 4: compound 4, PBS, pH=8.5, 3 h.
Figure 9A:
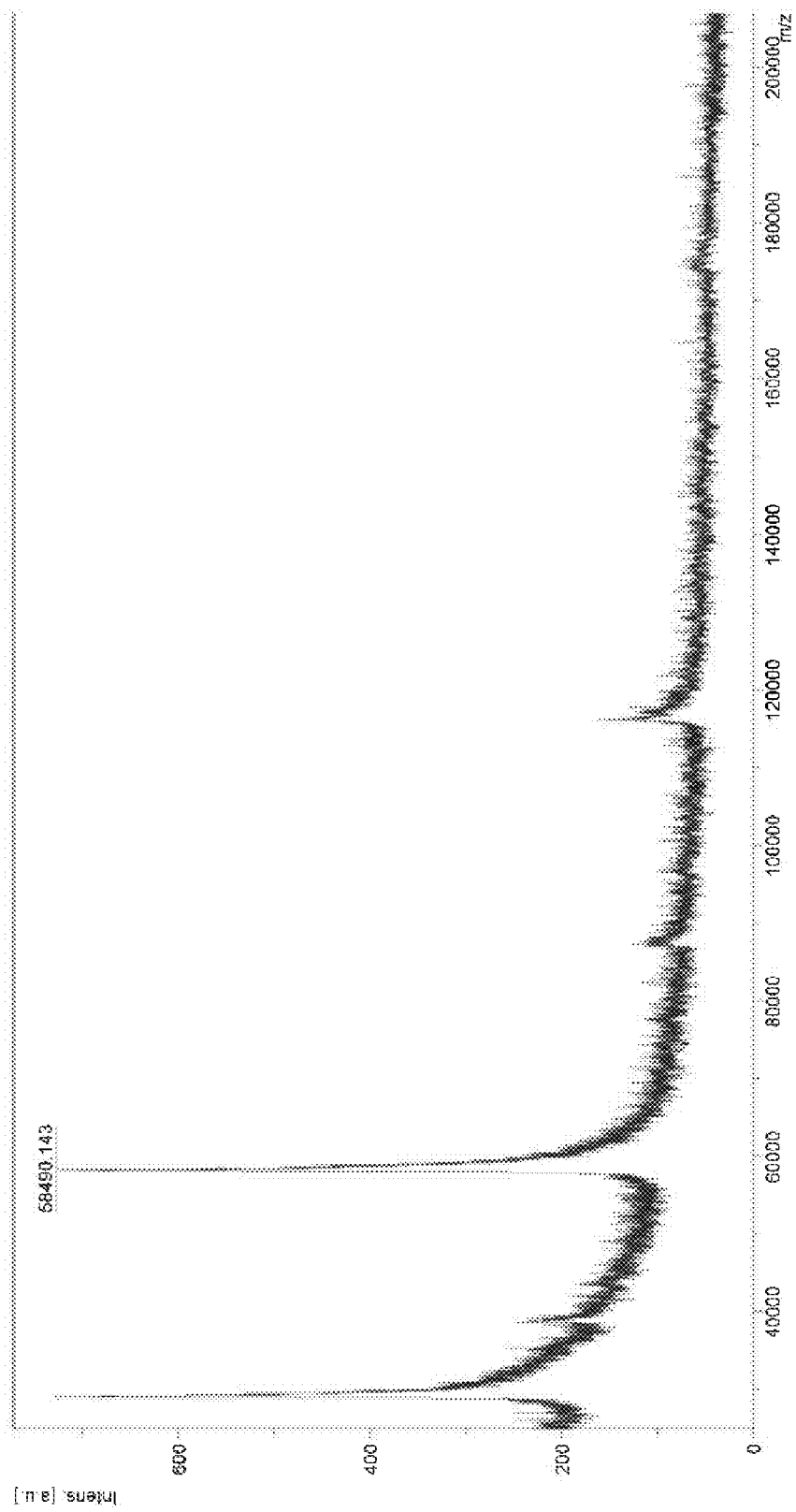
FIG. 9: MALDI-TOF analysis of A) $CRM_{197}$ (blue, 58.5 kDa), B) $CRM_{197}$-iodoacetamide (red, 68 kDa) and C) $CRM_{197}$-GPI conjugate of compound 4 with $CRM_{197}$ (black, 72 kDa); D) Comparison of the MALDI-TOF analyses of $CRM_{197}$ (blue, 58.5 kDa), $CRM_{197}$-iodoacetamide (red, 68 kDa) and $CRM_{197}$-GPI conjugate of compound 4 with $CRM_{197}$ (black, 72 kDa). As a Matrix 2',4',6'-Trihydroxyacetophenone (THAP) was used.
Figure 9B:
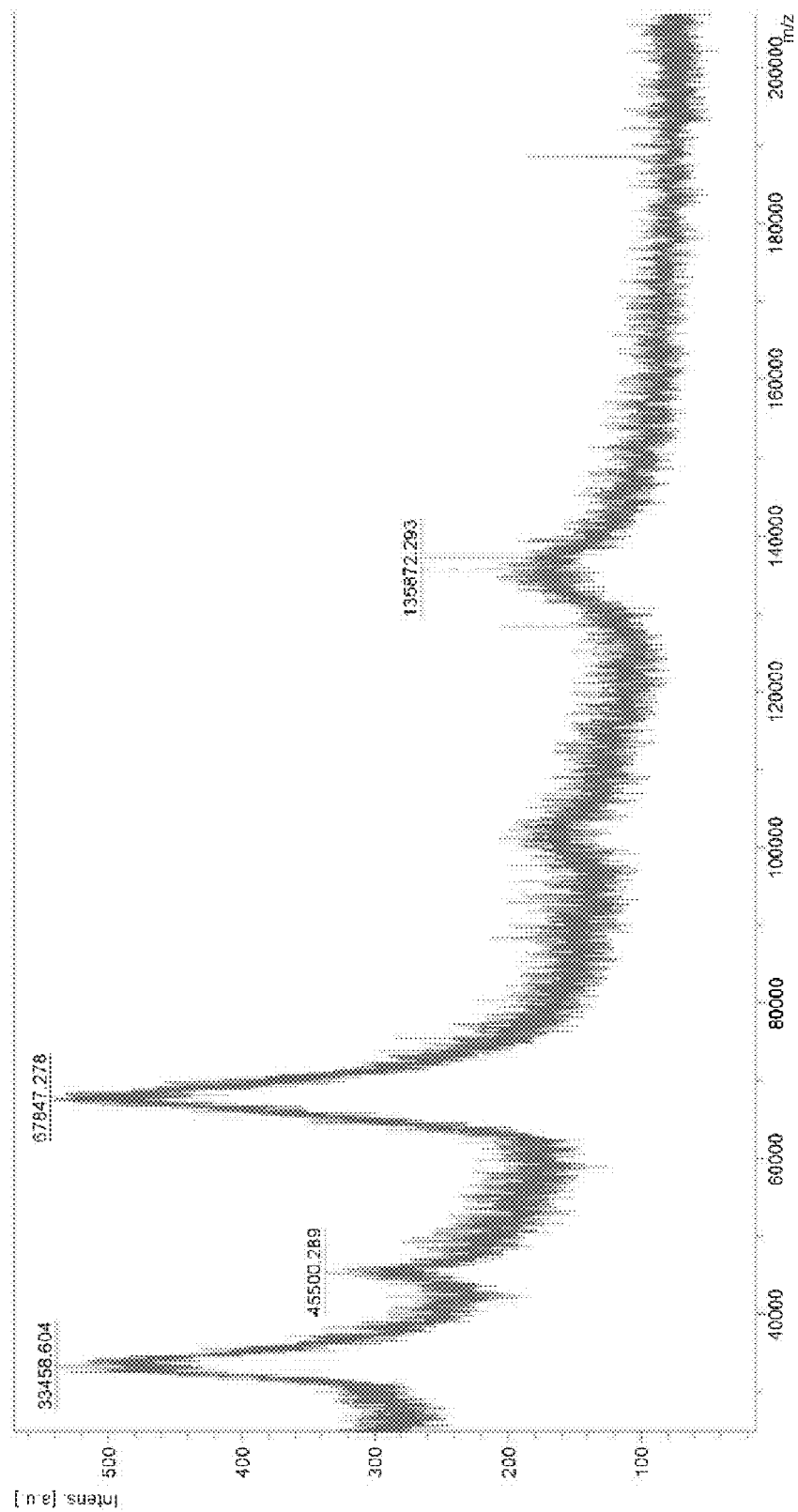
Figure 9C:
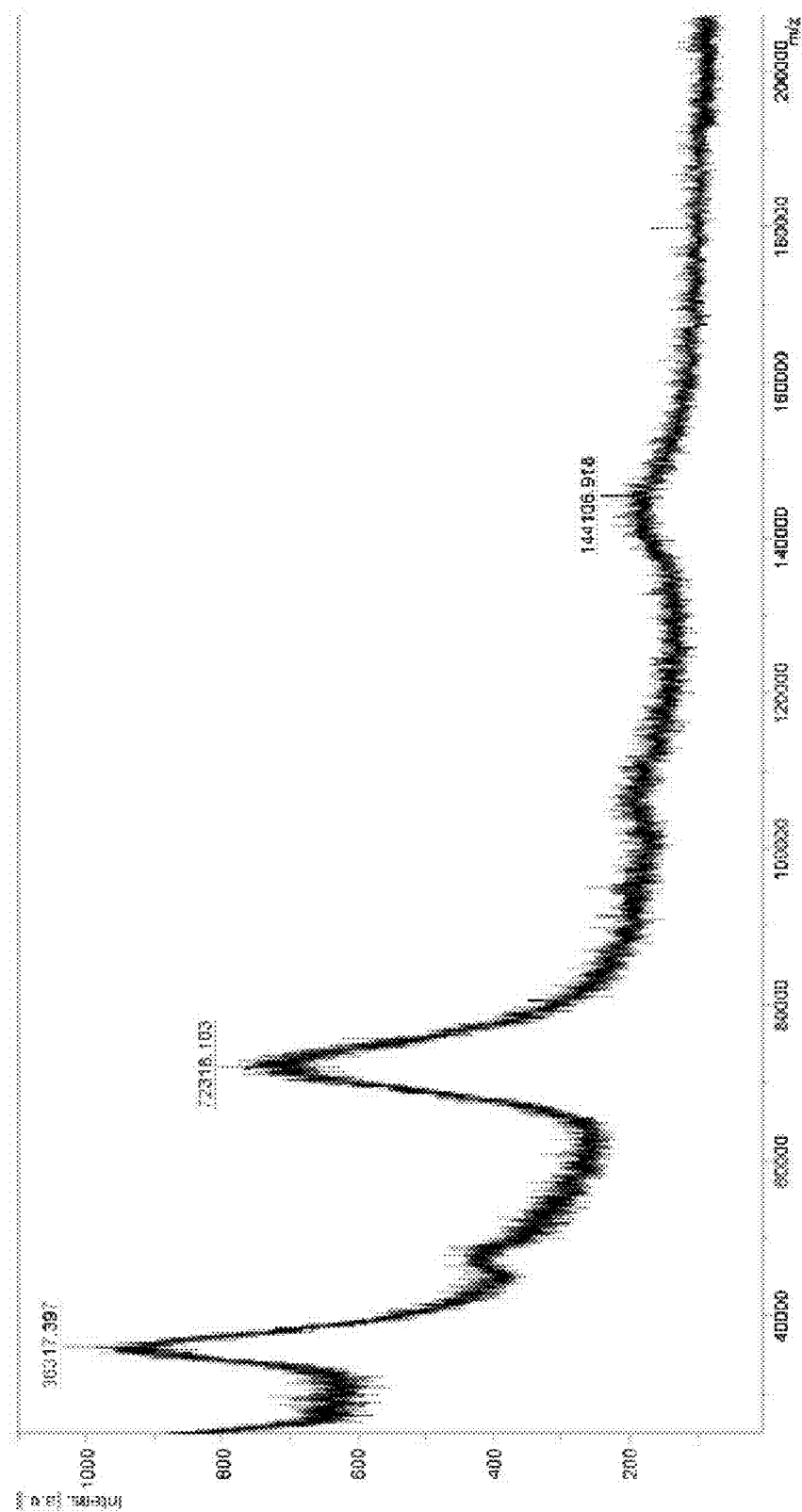
Figure 9D:
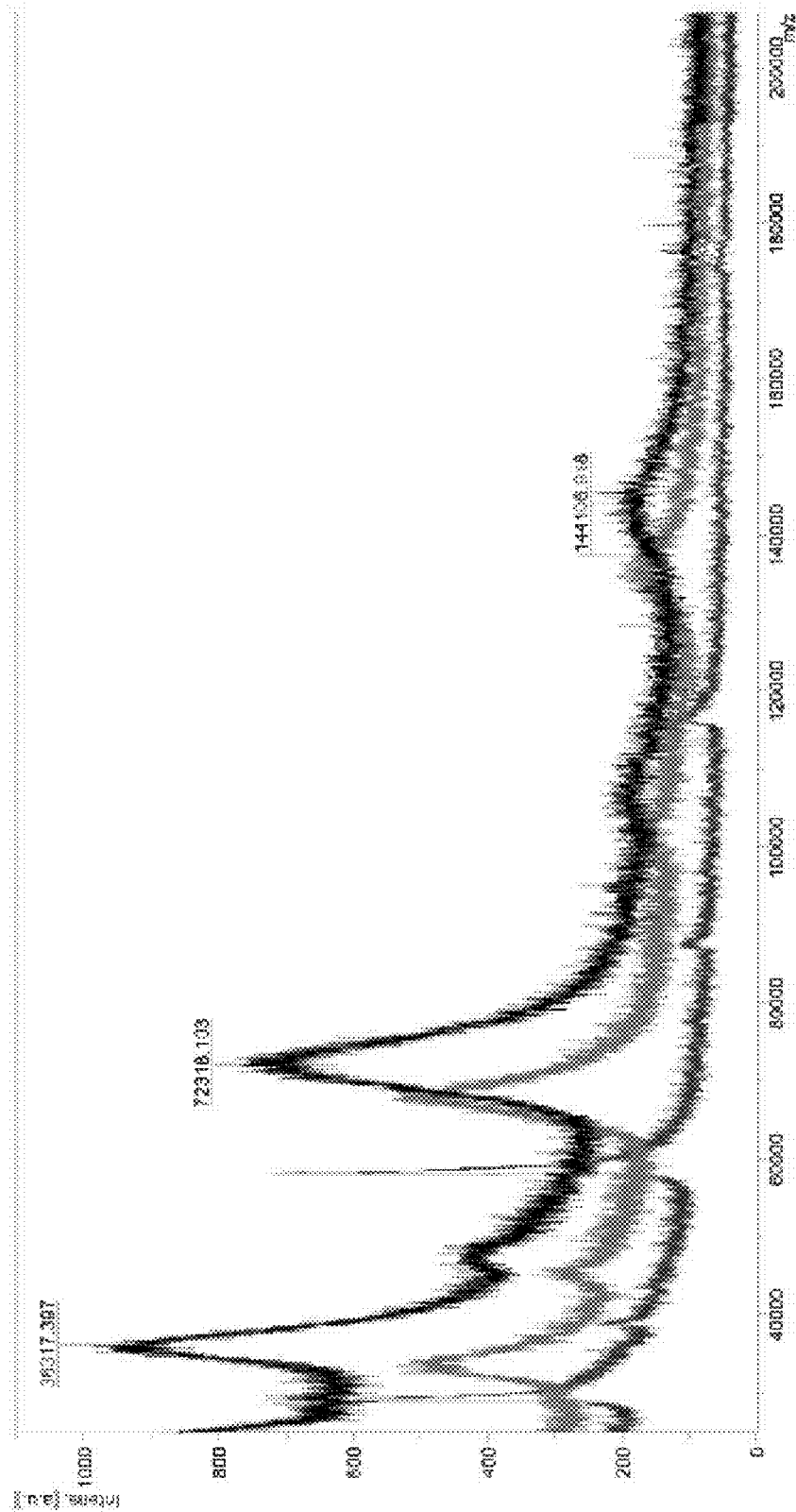

Conjugation of the compound 4 to $CRM_{197}$ protein is performed as described in FIG. 8. $CRM_{197}$ (1 mg, 0.017 µmol) was dissolved in sterile filtered double-distilled water (1 mL) and transferred to an Amicon® Ultra-4 centrifugal filter unit (10 kDa cut-off). To wash away the additive sucrose the solution was concentrated to 200 µL, sterile filtered double-distilled water (800 µL) was added and the solution was concentrated again to 200 µL volume. Phosphate buffer (50 mM $NaH_2PO_4$, pH 8.5, 800 µL) was added to the solution, which was transferred to an eppendorf tube. Sulfo-SIAB (0.9 mg, 1.7 µmol, Thermo Scientific) was added to the solution, which was agitated for 1 h under the exclusion of light. To wash away unreacted linker the solution was concentrated to 200 µL. Sterile filtered double-distilled water (800 µL) was added and the solution was concentrated again to 200 µL volume. This step was repeated one time. Afterwards, PBS sodium phosphate (pH 8.5, 500 µL) was added to the solution, which was transferred to an eppendorf tube. Compound 4 (250 µg, 0.165 µmol; in 250 µL double-distilled water) that was already incubated for 1 h with an equimolar amount of TCEP.HCl (tris(2-carboxyethyl)phosphine hydrochlorid, Thermo Scientific) was added to the solution. The reaction mixture was agitated for 3 h under the exclusion of light, before a cysteine solution (30 µL, 310 mM) was added to quench unreacted iodoacetamine groups. The conjugate was concentrated again to 200 µL volume. Sterile filtered double-distilled water (800 µL) was added and the solution was concentrated again to 200 µL volume. This step was repeated one time. Sterile filtered double-distilled water (800 µL) was added to the conjugate solution, which was divided in four aliquots of 250 µL each and lyophilized. The white powder was stored at −25° C. before use. Maldi-TOF analysis shows the formation of the target conjugate and that on average three compounds 4 were covalently linked to one carrier protein (see FIG. 9).

Figure 10:
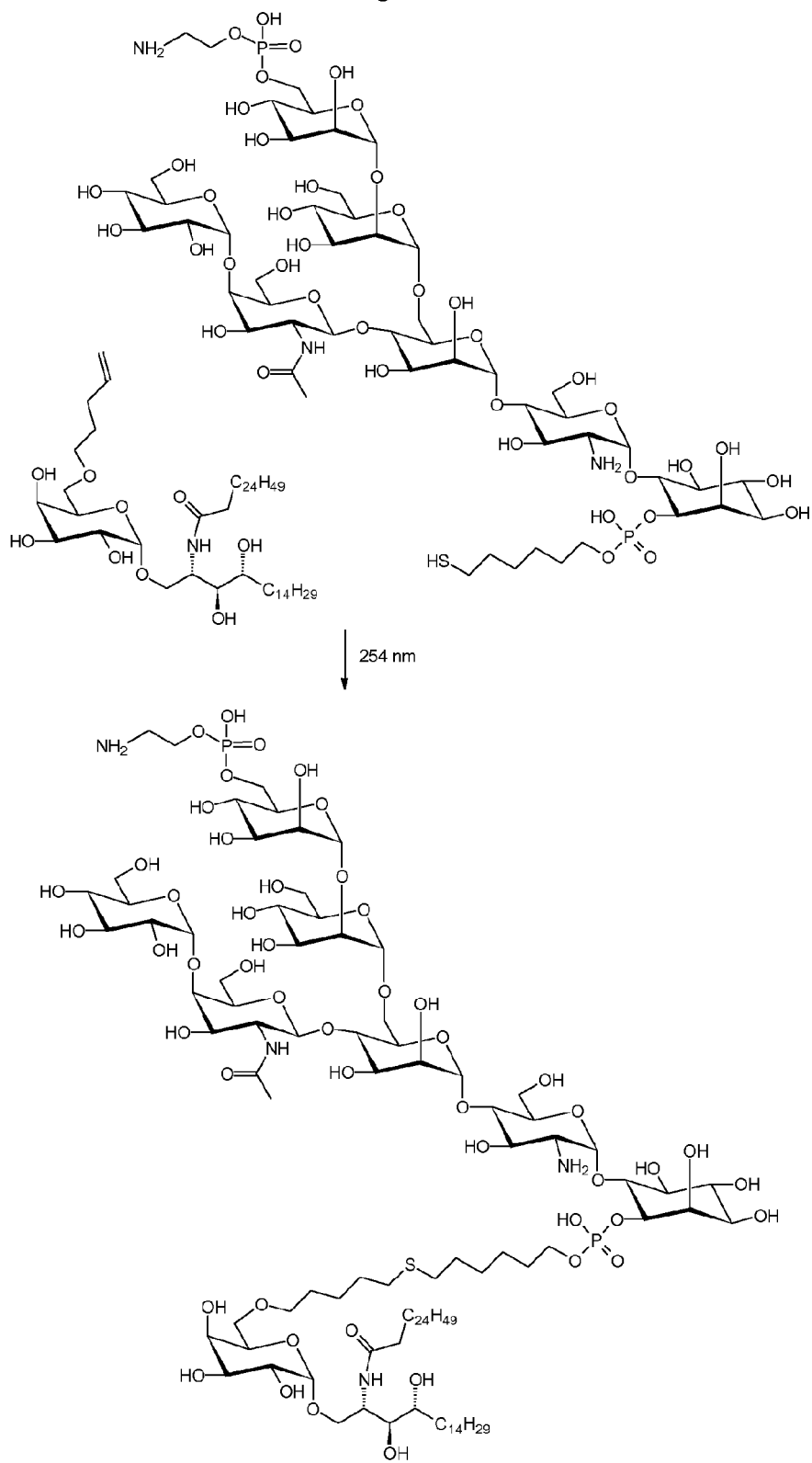
FIG. 10: In flow preparation of the conjugate of compound 4 with a vinyl-modified glycosphingolipid with immunomodulatory properties.

Example 11f: In Flow Conjugation of the Compound 4 to a Vinyl-Modified Glycosphingolipid with Immunomodulatory Properties By using a photochemical flow reactor (Chem. Eur. J. 2013, 19, 3090) that was fitted with a loop of Teflon AF2400 tubing (566 μL), a solution of compound 4 (1.5 equiv.) in water (300 μL) was reacted with pentenyl modified (2S,3S, 4R)-1-(α-D-galactopyranosyl)-2-hexacosanoylaminoocta-decane-3,4-diol (1 equiv.) in water (300 μL) and AcOH (8 μL; residence time: 10 min, flow rate: 28.3 μL/min$^{-1}$ per syringe) (see FIG. 10). The reactor output was lyophilized and the crude material was purified using size exclusion chromatography (Sephadex-G25, 5% EtOH in water, 10 mm×150 mm) to yield the conjugate of compound 4 covalently linked to the pentenyl modified (2S,3S,4R)-1-(α-D-galactopyranosyl)-2-hexacosanoylaminooctadecane-3,4-diol as white solid.

Figure 3:
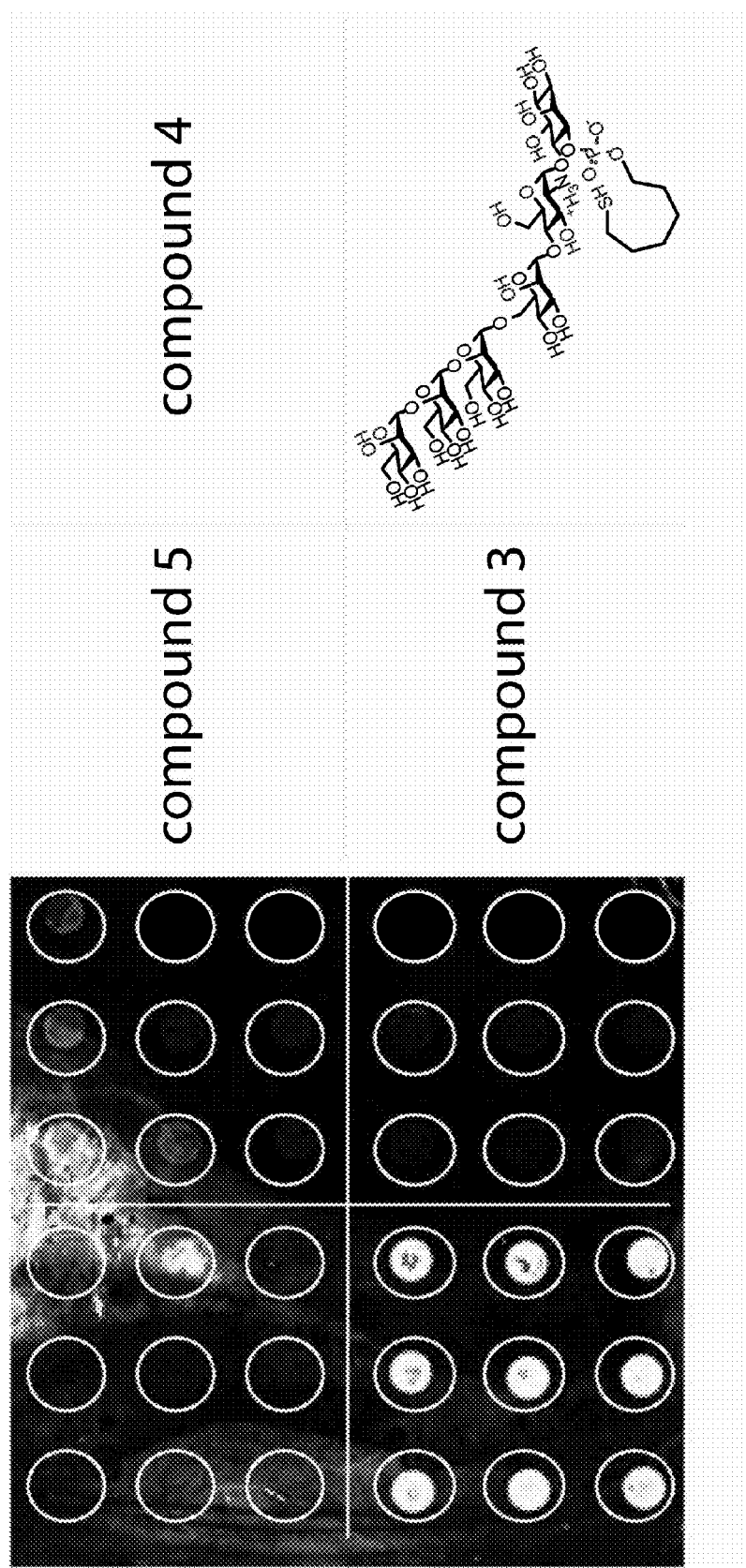
FIG. 3: left side: Analysis of pooled serum that was obtained 4 weeks after $1^{st}$ immunization of Balb/c mice with a conjugate consisting of $CRM_{197}$ covalently linked to compound 3; right side: Printing pattern: all compounds were printed in a 3×3 pattern and in a concentration of 1 mM; left, upper corner: compound 5; left lower corner: compound 3; right, upper corner: compound 4; right lower corner: (α-D-Mannopyranosyl)-(1→2)-(α-D-mannopyranosyl)-(1→2)-(α-D-mannopyranosyl)-(1→6)-(α-D-mannopyranosyl)-(1→4)-(2-amino-2-deoxy-α-D-glucopyranosyl)-(1→6)-1-O-(6-thiohexyl phosphono)-D-myo-inositol (*Chem. Eur. J.* 2005, 11, 2493). From the fluorescence pattern it can be seen that such specific antibodies were produced by the mouse that these antibodies specifically evoke a binding to compound 3, and not to the structurally very related compounds 4, 5 and (α-D-Mannopyranosyl)-(1→2)-(α-D-mannopyranosyl)-(1→2)-(α-D-mannopyranosyl)-(1→6)-(α-D-mannopyranosyl)-(1→4)-(2-amino-2-deoxy-α-D-glucopyranosyl)-(1→6)-1-O-(6-thiohexyl phosphono)-D-myo-inositol.

Example 12: Immunizations with the Conjugate Consisting of Compound 3 Covalently Linked to CRM$_{197}$ Protein Three female BALB/c mice were immunized s.c. with 35 μg conjugate, prepared as described in example 11a, in Freund's complete adjuvant. All mice were boosted two times with 35 μg conjugate in Freund's incomplete adjuvant in two-week intervals. After the second immunization, serum was collected and the antibody titer (total IgG) was determined by microarray six weeks after the first immunization. The results are shown in FIG. 3.

Example 13: Detection of *T. gondii* GPIs by Indirect Immunofluorescence

Figure 4:
FIG. 4: Fluorescence microscopic image of tachyzoiten stained with serum that was obtained after immunization of Balb/c mice with a conjugate consisting of compound 3 covalently linked to $CRM_{197}$; blue: cell nucleus, DAPI; green: fluorescent secondary antibody. The fluorescence image shows that the mouse serum which was derived from a mouse immunized with a conjugate consisting of compound 3 covalently linked to $CRM_{197}$ effectively binds to tachyzoites of *T. gondii*.
Figure 5:
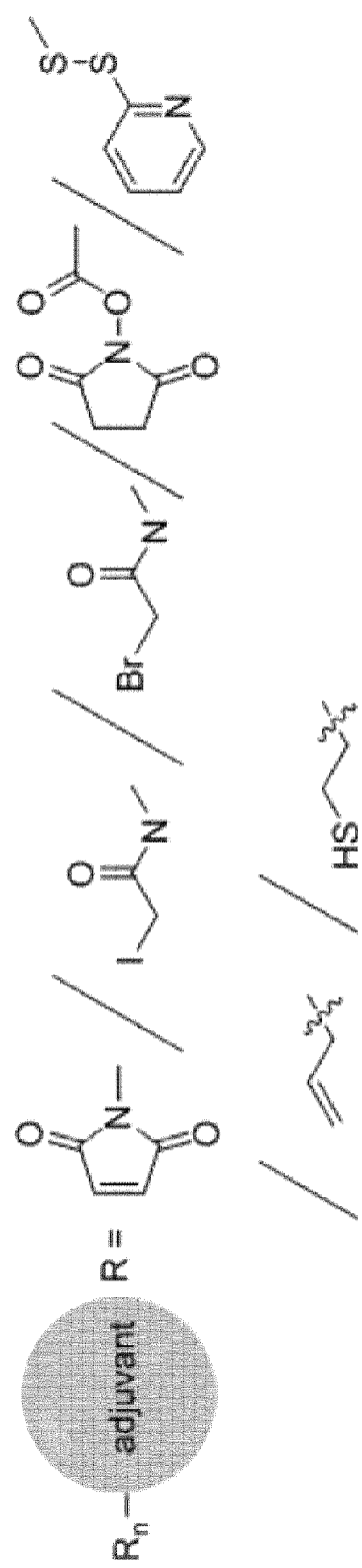
FIG. 5: A) Possible functional groups X being attached to a suitable carrier; B) Possible reaction pathway of attaching a compound of the general formula (I) to a carrier modified with a vinyl functional group X by an thiol-ene reaction upon activation by irradiation of light and/or by a radical starter.
Figure 5:
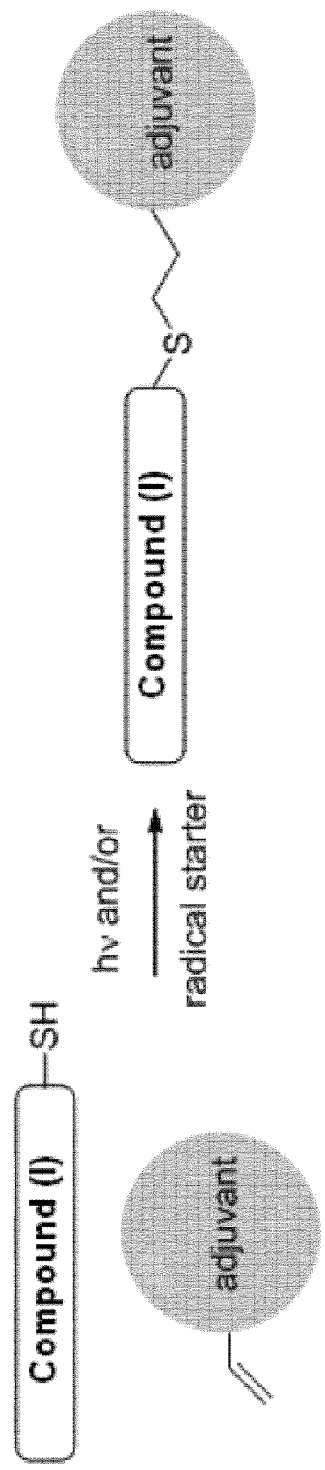

Extracellular tachyzoites collected from cell culture supernatants were fixed with 4% (w/v) paraformaldehyde in PBS for 30 min. Cells were washed three times with PBS, and incubated for 1 h with mice sera raised against compounds 3 or 4 diluted to 100 in PBS, 10% BSA. Cells were washed three times with PBS before incubated for 1 h with secondary FITC-conjugated anti-mouse immunoglobulin antibody (DakoCytomation, Glostrup) containing 10% BSA and washed finally three times with PBS. After three final washes with PBS, aliquot were spotted on microscope slides followed by a glass cover slides, mounted in Fluoroprep (Dako) and recorded by using a 100× Plan-NeoFluar oil objective lens with NA 1.30 using an Axiophot microscop (Zeiss). The results are shown in FIG. 4.

Figure 11:
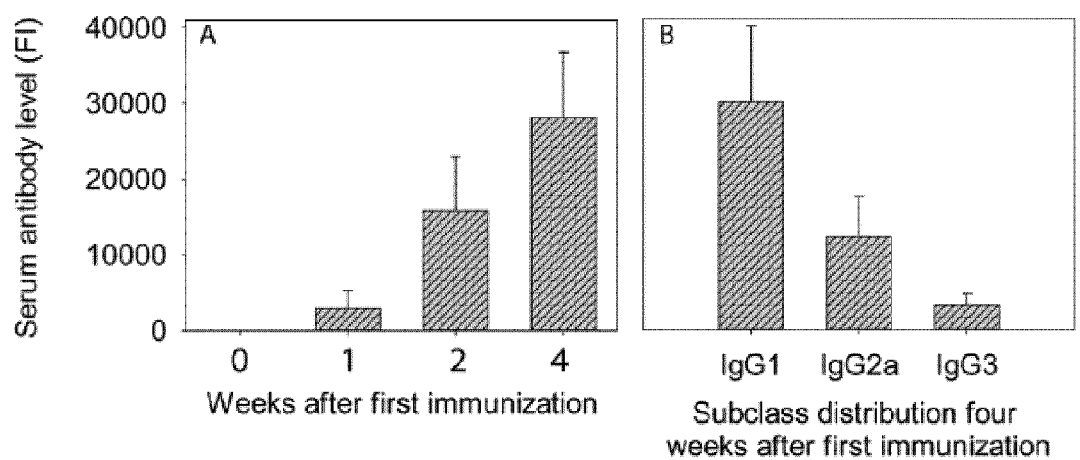
FIG. 11: Serum antibody levels against compound 4 in mice immunized with the conjugate obtained as described in example 11e: A) Total serum IgG levels; B) IgG subclass levels; Bars represent mean values averaged over all mice including standard error of the mean; FI=fluorescence intensity.

Example 14: Immunizations with the Conjugate Consisting of Compound 4 Covalently Linked to CRM$_{197}$ Protein To evaluate the immunogenic properties of the conjugate consisting of compound 4 covalently linked to CRM$_{197}$ protein, obtained as described at example 11e, BALB/c mice were immunized and boosted two times with 35 μg conjugate (in each case) in Freund's incomplete adjuvant in two-week intervals. The conjugate proved immunogenic in all mice and immunoglobulin (Ig) class-switching and affinity maturation were detected by carbohydrate microarray analysis (see FIG. 11A). IgG antibodies against compound 4 were detected up to a dilution of 1:1000 in sera of all mice six weeks after the first immunization. The nature of the IgG response was further evaluated, demonstrating that antibodies raised against compound 4 mainly consisted in IgG$_1$ and IgG$_{2a}$ subclasses, while IgG$_3$ was almost indetectable (see FIG. 11B), which is in agreement with previous results (*Infect. Immun.* 1999, 67, 4862). The high abundance of IgG$_{2a}$, which exhibits strong antibody-dependent cellular and complement-dependent cytotoxicity, suggests that the immune response to the conjugate of compound 4 to CRM$_{197}$ can induce phagocytosis or lysis of the parasite in vivo, assuming that the antibodies recognize the natural antigen on *T. gondii* cells.

Example 15: Specificity and Epitope Recognition of the Antibody Response Against Compound 4

Figure 12:
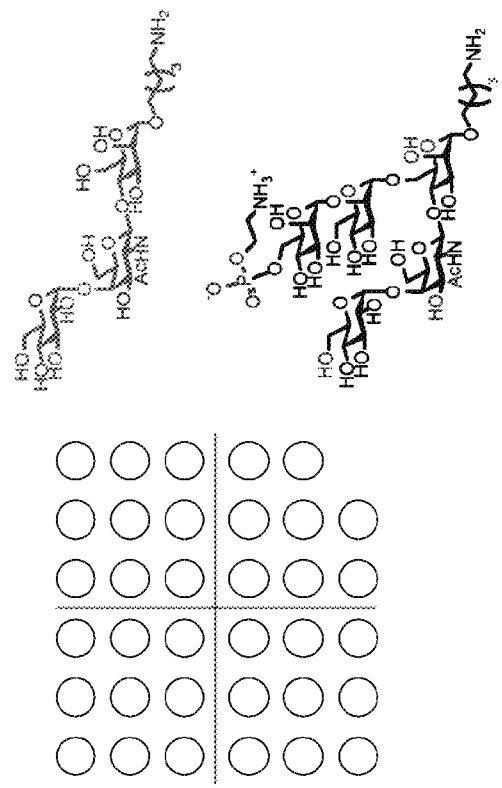
FIG. 12: Specificity and epitope recognition of the antibody response: Pictures of microarrays incubated with serum (dilution 1:1000) of the three mice six weeks after 1st immunization and a secondary fluorescent antibody directed against mouse IgG. Compound 4 as well as the shown substructures were printed at 100 μM.
Figure 12:
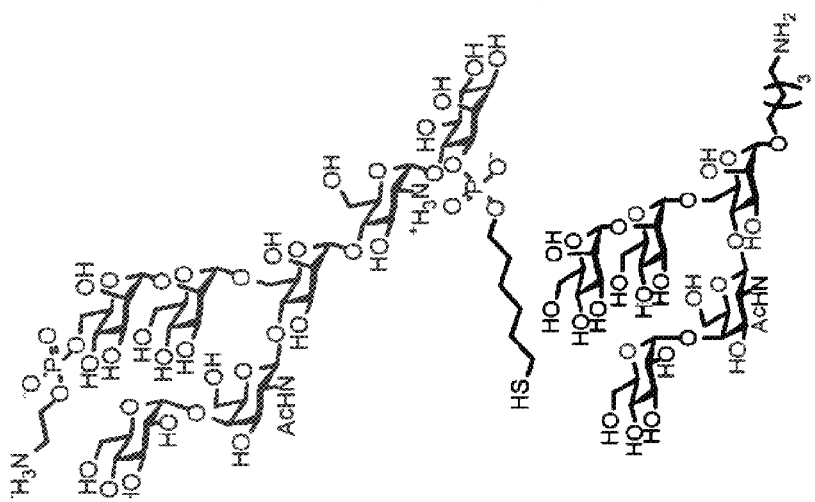
Figure 12:
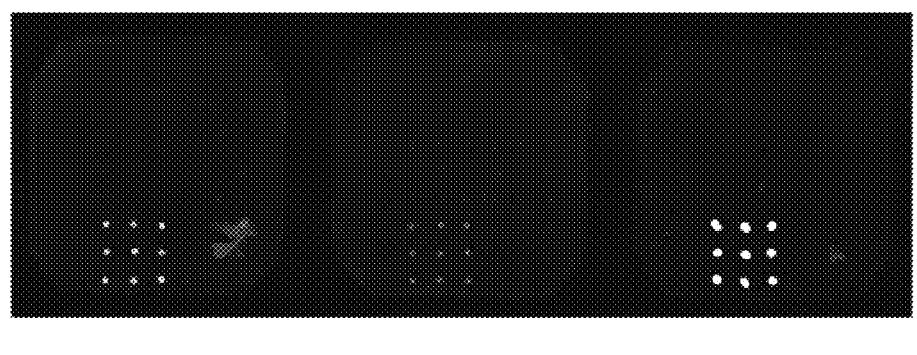

To address the specificity and epitope recognition of the antibody response, carbohydrate microarray analysis with substructures of compound 4 was employed (see FIG. 12). The immune response to all animals was highly specific towards compound 4, as antibodies did not recognize any of the substructures of compound 4 (see FIG. 12) at a dilution of 1:1000. This indicates a possible conformational change induced by the α-GcNH$_2$-(1→6)-myo-Ino moiety that affects the whole glycan 4, since none of the substructures contains this element. Therefore, the structural conformation of compound 4 likely differs from the analyzed substructures, which could explain the preference of the polyclonal antibodies. Another explanation for this specificity might be that the raised antibody recognizes multiple epitopes on compound 4. Hence the avidity of IgGs is significantly lower when one or more structural features are not present.

Example 16: Recognition of the Natural GPI Antigen Displayed on the *T. gondii* Parasite by the Antibodies Raised Against Compound 4

Figure 13:
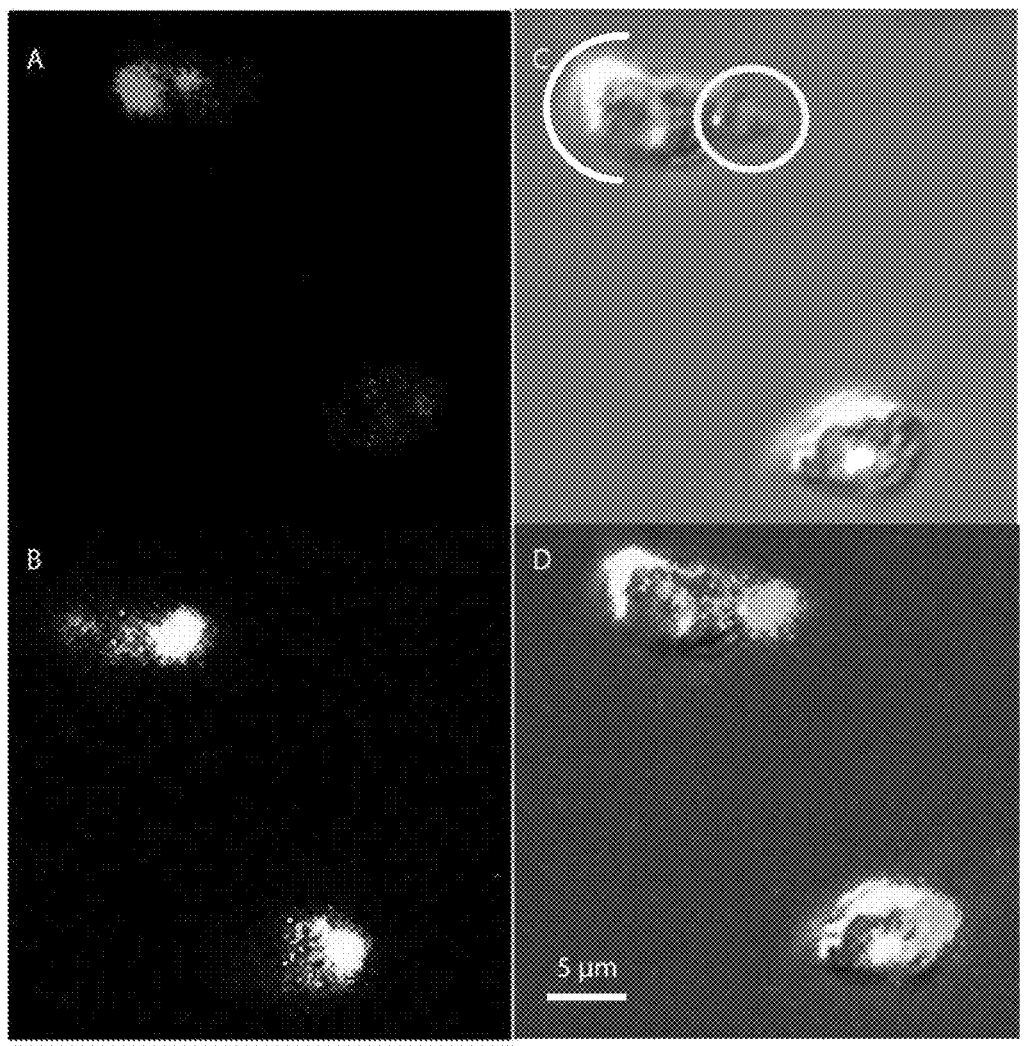
FIG. 13: Recognition of the natural GPI antigen displayed on the *T. gondii* parasite by the antibodies raised against compound 4: IF pictures of paraformaldehyde-fixed purified *T. gondii* tachyzoites grown in human foreskin fibroblasts stained with (A) DAPI (B) pooled serum from immunized mice and a secondary FITC-conjugated anti-mouse-IgG (C) differential interference contrast picture and (D) merge of (A), (B) and (C). Full circle in (C) indicates the apical and half circle the basolateral end of the parasite (white bar=5 μm).

To confirm that the antibodies raised against compound 4 recognize the natural GPI antigen displayed on the parasite, *T. gondii* tachyzoites were incubated with serum of immunized mice and analyzed with immunofluoresecence (IF) confocal microscopy (see FIG. 13). The antibodies bound to the surface of the parasite and showed preferential localization of the GPI containing the additional α-glucose in the side chain at the apical end of the cell. In contrast, antibodies binding to the parasite in sera of mice before immunization could not be detected. These results indicate that the GPI containing the additional α-glucose in the side chain potentially plays a role in the formation or function of the apical complex, which is essential for invasion of host cells and plays a critical role during replication of *T. gondii*. Tachyzoites secrete factors for attachment, invasion and formation of the parasitophorous vacuole, which is surrounding and protecting the parasite inside the host cell from endocytosis, in a regulated fashion from the apical region. Blocking the site of attachment with opsonizing antibodies directed against the GPI structure containing the α-Glc in the side chain and clustering of this antigen could disturb the organization of the apical membrane leading to inhibition of the cell invasion. This dual mechanism of action has great potential to induce sterile immunity against *T. gondii*

The invention claimed is:

1. A compound of a formula (I):

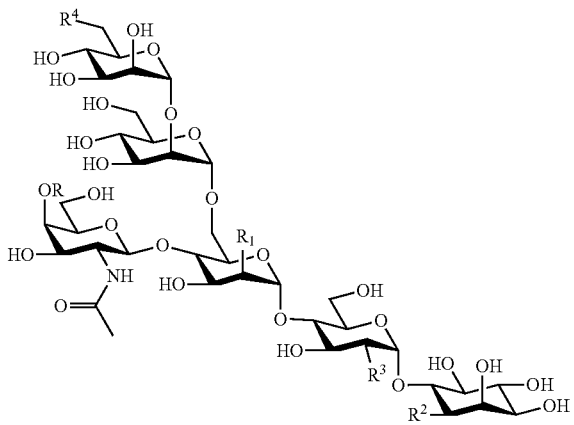

wherein
R represents

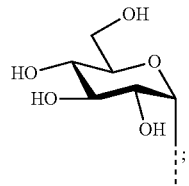

$R^1$ is —OH and $R^4$ is —OP(O)(OH)—O—X—NH$_2$;
X is selected from the group consisting of —CH$_2$—, —C$_2$H$_4$—, —C$_3$H$_6$—, —C$_4$H$_8$—, —C$_5$H$_{10}$—, and —C$_6$H$_{12}$—;
$R^2$ represents —OP(O)(OR$^5$)(OR$^6$);
$R^3$ is selected from the group consisting of —H, —OH, —NH$_2$, NHCOCH$_3$, —NHCOCH$_2$CH$_3$, —NHCOCH$_2$CH$_2$CH$_3$, and —N$_3$;
$R^5$ and $R^6$ are independently selected from the group consisting of —H, -L-SH, —(C$_2$H$_4$O)$_r$—CH$_2$—SH and —(C$_2$H$_4$O)$_r$—C$_2$H$_4$—SH, with the proviso that $R^5$ and $R^6$ cannot both be —H, and one of $R^5$ and $R^6$ is hydrogen;
L is a linking group; and
r is an integer of from 1 to 40.

2. The compound of claim 1, wherein $R^5$ is —H and $R^6$ is —C$_6$H$_{12}$—SH.

3. The compound of claim 1, covalently linked to a carrier.

4. The compound of claim 3, wherein the carrier is selected from the group consisting of a diphtheria toxoid, a mutated diphtheria toxoid, a modified diphtheria toxoid, and a tetanus toxoid.

5. The compound of claim 3, immobilized on a carrier material by covalent bonding.

6. The compound of claim 5, wherein the carrier material is selected from the group consisting of a glass slide, a microtiter plate, test tubes, microspheres, nanoparticles and beads.

7. A method of vaccination, comprising:
administering the compound of claim 3 to a patient, whereby the patient is vaccinated against toxoplasmosis.

8. A method of vaccination, comprising:
administering the compound of claim 4 to a patient, whereby the patient is vaccinated against toxoplasmosis.

9. A method of vaccination, comprising:
Administering the compound of claim 2 covalently linked to a carrier to a patient, whereby the patient is vaccinated against toxoplasmosis.

10. The compound of claim 1, having a formula:

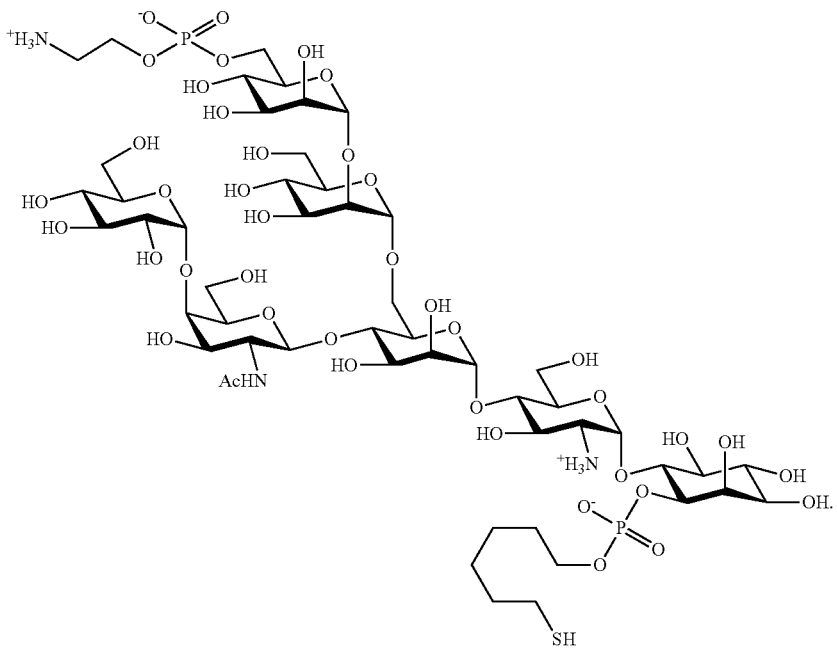

* * * * *